US008632768B2

(12) United States Patent
Ildstad et al.

(10) Patent No.: US 8,632,768 B2
(45) Date of Patent: Jan. 21, 2014

(54) HUMAN FACILITATING CELLS

(75) Inventors: Suzanne T. Ildstad, Prospect, KY (US); Mary Jane Elliott, Brandenburg, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 221 days.

(21) Appl. No.: 12/957,011

(22) Filed: Nov. 30, 2010

(65) Prior Publication Data

US 2011/0110909 A1  May 12, 2011

Related U.S. Application Data

(63) Continuation-in-part of application No. PCT/US2009/003340, filed on Jun. 1, 2009.

(60) Provisional application No. 61/057,724, filed on May 30, 2008, provisional application No. 61/374,460, filed on Aug. 17, 2010.

(51) Int. Cl.
*A61K 35/28* (2006.01)

(52) U.S. Cl.
USPC ....................................................... 424/93.7

(58) Field of Classification Search
None
See application file for complete search history.

(56) References Cited

U.S. PATENT DOCUMENTS

| 5,061,620 | A | 10/1991 | Tsukamoto et al. |
| 5,772,994 | A | 6/1998 | Ildstad et al. |
| 6,013,519 | A | 1/2000 | Ildstad et al. |
| 2004/0185043 | A1 | 9/2004 | Ildstad |
| 2004/0228845 | A1 | 11/2004 | Ildstad |
| 2005/0118142 | A1 | 6/2005 | Ildstad |
| 2007/0098693 | A1 | 5/2007 | Ildstad |

FOREIGN PATENT DOCUMENTS

| WO | WO 99/26639 | 6/1999 |
| WO | WO 2005/023982 | 3/2005 |

OTHER PUBLICATIONS

William R. Drobyski and David Majewski, Donor gamma delta T Lymphocytes Promote Allogeneic Engraftment Across the Major Histocompatibility Barrier in Mice, Feb. 1, 1997, Blood, vol. 89, No. 3, pp. 1100-1109.*
Gangopadhyay et al., "Bone marrow-derived CD8alpha+TCR- cells that facilitate allogeneic bone marrow transplantation are a mixed population of lymphoid and myeloid progenitors," *Experimental Hematology*, Oct. 17, 2007, 35(12):1847-1857.
Schuchert et al., "Characterization of a newly discovered t-cell receptor beta-chain heterodimer expressed on a CD8+ bone marrow subpopulation that promotes allogeneic stem cell engraftment," *Nat Med.*, Aug. 2000, 6(8):904-909.
Authorized Officer Sabine Novak-Giese, Supplementary European Search Report re EP 09 75 8732 completed Mar. 15, 2012, 9 pages.
Akpinar et al., "Measurement of chimerism in cynomolgus monkeys using human-specific short tandem repeat-based assay," *Transplantation*, 2005, 79:236-239.
Fugier et al., "Plasmacytoid precursor dendritic cells facilitate allogeneic hematopoietic stem cell engraftment," *J. Exp. Med.*, 2005, 201(3):373-383.

(Continued)

*Primary Examiner* — Blaine Lankford
*Assistant Examiner* — Trent R Clarke
(74) *Attorney, Agent, or Firm* — Fish & Richardson P.C.

(57) ABSTRACT

The present disclosure relates to human facilitating cells (hFC), and methods of isolating, characterizing, and using such hFCs.

7 Claims, 27 Drawing Sheets

(56) References Cited

OTHER PUBLICATIONS

Grimes et al., "Graft facilitating cells are derived from hematopoietic stem cells and functionally require CD3, but are distinct from T lymphocytes," *Exp. Hematol.*, 2004, 32:946-954.

Kaufman et al., "Phenotypic characterization of a novel bone marrow-derived cell that facilitates engraftment of allogeneic bone marrow stem cells," *Blood*, 1994, 84:2436-2446.

Patel et al., "Long-term outcomes of nonconditioned patients with severe combined immunodeficiency transplanted with HLA-identical or haploidentical bone marrow depleted of T cells with anti-CD6 mAb," *J. Allergy Clin. Immunol.*, 2008, 122:1185-1193.

Rezzoug et al., "TNF-alpha is critical to facilitate hemopoietic stem cell engraftment and function," *J. Immunology*, 2008, 180(1):49-57.

Sutherland et al., "The ISHAGE guidelines for CD34+ cell determination by flow cytometry," *J. Hematotherapy*, 1996, , 5:213-226.

Authorized Officer Kee-Yeun Kim, PCT/US2009/003340, International Search Report and Written Opinion of the International Searching Authority, mailed Nov. 10, 2009, 9 pages.

Authorized Officer Athina Nickitas-Etienne, PCT/US2009/003340, International Preliminary Report on Patentability, issued Nov. 30, 2010, 6 pages.

Bae et al., "Thy1-positive bone marrow stem cells express liver-specific genes in vitro and can mature into hepatocytes in vivo," *Hepatol Int*, (2008) 2:63-71.

Calloni et al., "Reviewing and Updating the Major Molecular Markers for Stem Cells," *Stem Cells and Development*, (2013) vol. 00, No. 00, pp. 1-22.

\* cited by examiner

US 8,632,768 B2

HUMAN FACILITATING CELLS

CROSS REFERENCE TO RELATED APPLICATIONS

This application is a Continuation-In-Part application of, and claims benefit under 35 U.S.C. §120 to, PCT/US09/003,340 filed Jun. 1, 2009, which claims benefit under 35 U.S.C. §119(e) to U.S. Application No. 61/057,724 filed May 30, 2008. This application also claims benefit under 35 U.S.C. §119(e) to U.S. Application No. 61/374,460 filed Aug. 17, 2010.

FEDERALLY SPONSORED RESEARCH OR DEVELOPMENT

This invention was made with government support under Grant No. 062016 awarded by the WM KECK Foundation and Grant No. W81XWH-07-0185 awarded by the Department of Defense Office of Army Research. The government has certain rights in the invention.

TECHNICAL FIELD

This invention relates to human facilitating cells, and the use of such cells in therapeutic protocols.

BACKGROUND

Facilitating cells (FCs) from mouse have been described. See, for example, U.S. Pat. No. 5,772,994. FCs are not stem cells, but significantly improve the initial and long-term engraftment of stem cells. For example, transplantation of stem cells alone only prolongs survival of a transplant patient, while the presence of FCs result in sustained and long-term HSC engraftment. See, also, Kaufman et al., 2005, *J. Exp. Med.*, 201:373-83).

SUMMARY

The present invention relates to human facilitating cells (hFCs), methods of isolating hFCs, and methods of using hFCs for facilitating reconstitution of a damaged or destroyed hematopoietic system with stem cells as well as for inducing donor-specific tolerance for the transplantation of donor cells, tissues and solid organs.

In one aspect, a cellular composition comprising is provided. Such a cellular composition can include at least about 30% (e.g., at least about 40%, at least about 50%, or at least about 60%) human facilitating cells (hFCs), wherein the hFCs comprise cells having a phenotype of CD8+/alpha beta TCR−/CD56$^{dim/neg}$ and cells having a phenotype of CD8+/alpha beta TCR−/CD56$^{bright}$.

In some embodiments, the cells have a phenotype of CD8+/alpha beta TCR−/CD56$^{dim/neg}$ are predominantly CD3 epsilon+/CD19−. In some embodiments, the cells have a phenotype of CD8+/alpha beta TCR−/CD56$^{bright}$ are predominantly CD3 epsilon−/CD19+. In some embodiments, the hFCs include cells having a phenotype of CD8+/alpha beta TCR−/delta gamma TCR+/CD3 epsilon+/CD19+. In some embodiments, the hFCs include cells having a phenotype of CD8+/alpha beta TCR−/B220+/CD11c+/CD11b−. In some embodiments, about 48% of the hFCs are CD8+/alpha beta TCR−/CD3 epsilon+, about 33% of the hFCs are CD8+/alpha beta TCR−/CD19+, about 44% of the hFCs are CD11c+, about 40% of the hFCs are CD11b+, about 42% of the hFCs are Foxp3, and about 30% of the hFCs are HLA-DR.

In some embodiments, about 25% of the hFCs are CD8+/alpha beta TCR−/IFN-gamma and about 31% of the hFCs are CD8+/alpha beta TCR−/CXCR4.

In one aspect, a therapeutic cellular composition is provided. Such a therapeutic cellular composition can include human hematopoietic stem cells (HSCs), wherein the HSCs have a phenotype of CD34+; human facilitating cells (hFCs), wherein the hFCs comprise cells having a phenotype of CD8+/alpha beta TCR−/CD56$^{dim/neg}$ and cells having a phenotype of CD8+/alpha beta TCR−/CD56$^{bright}$; and human alpha beta TCR+ T cells, wherein the alpha beta TCR+ T cells are present in an amount that is greater than would be considered therapeutic. In some embodiments, the therapeutic cellular composition is for delivery to a recipient. Also in some embodiments, the alpha beta TCR+ T cells are present in an amount between about $2.0 \times 10^6$ and about $5.0 \times 10^6$ alpha beta TCR+ T cells/kg recipient body weight. In some embodiments, the number of alpha beta TCR+ T cells are adjusted to between about $2.0 \times 10^6$ and about $5.0 \times 10^6$ alpha beta TCR+ T cells/kg recipient body weight. In some embodiments, the number of alpha beta TCR+ T cells are adjusted to between about $3.0 \times 10^6$ and about $4.2 \times 10^6$ alpha beta TCR+ T cells/kg recipient body weight.

In one aspect, a method of making a therapeutic cellular composition for delivery to a recipient is provided. Such a method typically includes providing a donor source of hematopoietic stem cells (HSCs); depleting alpha beta TCR+ T cells from the donor source to produce a depleted donor source; adjusting the number of alpha beta TCR+ T cells in the depleted donor source to greater than $1 \times 10^5$ alpha beta TCR+ T cells per kg recipient body weight, thereby producing a therapeutic cellular composition for delivery to a recipient. In some embodiments, the source of HSCs is bone marrow, thymus, peripheral blood, fetal liver, or embryonic yolk sac. In certain embodiments, the T cells are depleted using one or more antibodies. In some embodiments, the one or more antibodies are conjugated to magnetic beads. It is a feature of the disclosure that the hFCs described herein improve the engraftment ability of the HSCs compared to HSCs engrafted in the absence of the hFCs In one aspect, a method of making the immune system of a recipient chimeric with the immune system of a donor is provided. Such a method typically includes administering the therapeutic cellular composition described above to the recipient, wherein the recipient has been conditioned.

In some embodiments, the conditioning of the recipient includes a dose of total body irradiation (TBI), wherein the total body irradiation does not exceed 300 cGy. In some embodiments, the therapeutic cellular composition is administered to the recipient intravenously. In some embodiments, the recipient's immune system is considered to be chimeric with the donor's immune system when the recipient's immune system is at least about 1% donor origin.

In some embodiments, the recipient has a disease. For example, the disease can be an autoimmune disease, leukemia, a hemoglobinopathy, an inherited metabolic disorder, or a disease that necessitates an organ transplant. Representative autoimmune diseases include diabetes, multiple sclerosis, and systemic lupus erythematosus. In some embodiments, the disease is an infection by an immunodeficiency virus or hepatitis. In some embodiments, the disease can be a hematopoietic malignancy, anemia, hemoglobinopathies, or an enzyme deficiency. In some embodiments, the transplanted organ is heart, skin, liver, lung, heart and lung, kidney, pancreas, or an endocrine organ (e.g., a thyroid gland, parathyroid gland, a thymus, adrenal cortex, or adrenal medulla).

In one aspect, a cellular composition is provided that includes at least about 30% human facilitating cells (hFCs) having a phenotype of CD8+/TCR−/CD56$^{dim/neg}$. Such a cellular composition further can include hematopoietic stem cells (HSCs), wherein the HSCs have a phenotype of CD34+, wherein the HSCs are MHC-matched with the hFCs. In another aspect, a cellular composition is provided that includes human hematopoietic stem cells (HSCs), wherein the HSCs have a phenotype of CD34+; and human facilitating cells (hFCs), wherein the hFCs have a phenotype of CD8+/TCR−/CD56$^{dim/neg}$. In one embodiment, the hFCs CD56$^{dim/neg}$ phenotype is CD56$^{dim}$.

According to this disclosure, hFCs further can have a phenotype of CD3+/CD16+/CD19+/CD52+. In addition, hFCs can have a phenotype, without limitation, of CXCR4, CD123, HLADR, NKp30, NKp44, NKp46, CD11c, and CD 162, and hFCs further can be characterized by the presence of markers such as, without limitation, CD11a, CD11b, CD62L, and FoxP3. Typically, the hFCs described herein improve the engraftment ability of the HSCs compared to HSCs engrafted in the absence of the hFCs. Cellular compositions as described herein can include at least about 50% (e.g., 75%, or 90%) of the hFCs. Typically, the phenotype of the cells is determined by antibody staining or flow cytometry.

In one aspect, a pharmaceutical composition is provided that includes a cellular composition as described herein. In another aspect, methods of treating a human suffering from a disease are provided. Such methods generally include administering a pharmaceutical composition that includes a cellular composition as described herein to a human. In still another aspect, methods of transplanting donor cells, tissues, or organs into a human recipient are provided. Such methods generally include administering a pharmaceutical composition that includes a cellular composition as described herein to the human recipient.

Such methods can further include partially conditioning the human by exposure to total body irradiation, an immunosuppressive agent, a cytoreduction agent, or combinations thereof prior to the administration of the pharmaceutical composition. In one embodiment, the total body irradiation is 200 cGy. A pharmaceutical composition as described herein can be administered intravenously.

In one embodiment, the disease is an autoimmune disease such as diabetes, multiple sclerosis, or systemic lupus erythematosus. In another embodiment, the disease is an infection by an immunodeficiency virus or hepatitis. In yet another embodiment, the disease is chosen from a hematopoietic malignancy, anemia, hemoglobinopathies, and an enzyme deficiency.

Representative donor tissues or organs include, without limitation, heart, skin, liver, lung, heart and lung, kidney, pancreas, or an endocrine organ such as a thyroid gland, parathyroid gland, a thymus, adrenal cortex, or adrenal medulla. Donor cells can be pancreatic islet cells, neurons, or myocytes.

In yet another aspect, methods for obtaining a cellular composition that includes at least about 0.5% to 8.0% hFCs is provided. Such a method generally includes providing a hematopoietic cell composition; and removing cells from the hematopoietic cell composition that have a phenotype of alpha beta TCR− and gamma delta TCR−. Such methods can further include selecting for cells that have a phenotype of CD8+; selecting for cells that have a phenotype of CD56$^{dim/neg}$; and selecting for cells that have a phenotype of CD3+/CD16+/CD19+/CD52+. In addition, such methods can further include selecting for cells that have a phenotype of CXCR4, CD123, HLADR, NKp30, NKp44, NKp46, CD11c, and CD162, and such methods can still further include selecting for cells that have a phenotype of, without limitation, CD11a, CD11b, CD62L, and FoxP3. A cellular composition produced by such methods also can include CD34+ hematopoietic stem cells (HSCs).

Cells can be removed and/or selected for using an antibody (e.g., an antibody conjugated to a magnetic bead). In addition or alternatively, the hematopoietic cell composition can be separated by density gradient centrifugation to obtain cells in the mononuclear cell fraction. In one embodiment, the hematopoietic cell composition is contacted with a growth factor. The hematopoietic cell composition can be obtained from bone marrow, thymus, peripheral blood, fetal liver, or embryonic yolk sac. In one embodiment, cellular composition includes at least about 50% hFCs (e.g., at least about 75% hFCs).

Unless otherwise defined, all technical and scientific terms used herein have the same meaning as commonly understood by one of ordinary skill in the art to which this technology belongs. Although methods and materials similar or equivalent to those described herein can be used in the practice or testing of the present methods and compositions, suitable methods and materials are described below. In addition, the materials, methods, and examples are illustrative only and not intended to be limiting. All publications, patent applications, patents, and other references mentioned herein are incorporated by reference in their entirety.

The details of one or more embodiments of the invention are set forth in the accompanying drawings and the description below. Other features, objects, and advantages will be apparent from the drawings and detailed description, and from the claims.

DETAILED DESCRIPTION

Human hFCs (hFCs) are provided that facilitate initial stem cell engraftment and that are required for sustained HSC engraftment. Also provided are methods of purifying such hFCs from bone marrow or other physiological sources of hematopoietic cells. A variety of separation procedures are provided, which generally are based on the presence or absence of specific markers as disclosed herein.

Figure 1:
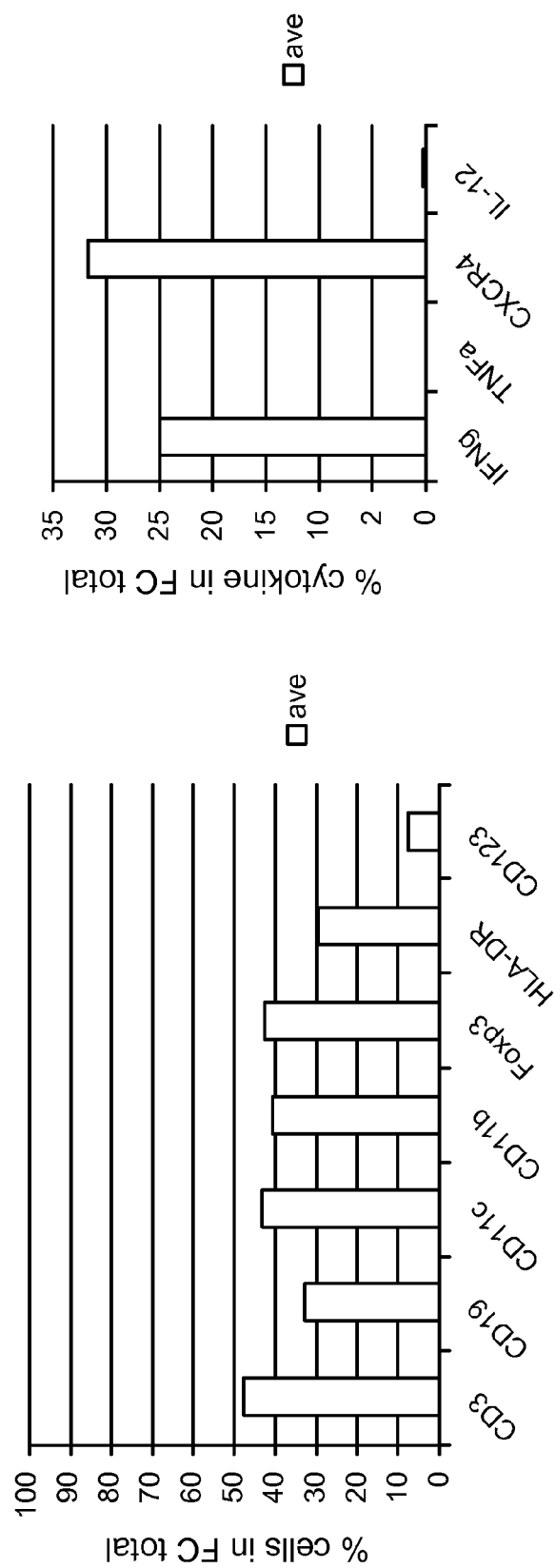
FIG. 1 are graphs showing representative phenotypic analysis of hFCs.

Human Facilitating Cells (hFCs), Cellular Compositions Containing hFCs, and Methods of Making Human facilitating cells (hFCs) have been identified and are described herein. hFCs are generally characterized as CD8+ and alpha beta TCR−. hFCs also can be gamma delta TCR− or gamma delta TCR+ (i.e., the absence of gamma delta TCR cells is not required). The CD8+/alpha beta TCR− hFCs can be characterized by the presence of cells expressing the following markers: CD3 epsilon (expressed by about 48% of hFCs), CD19 (expressed by about 33% of hFCs), CD11c (expressed by about 44% of hFCs), CD11b (expressed by about 40% of hFCs), Foxp3 (expressed by about 42% of hFCs), HLA-DR (expressed by about 30% of hFCs), and CD123 (expressed by about 8% of hFCs) (FIG. 1A). hFCs also can be characterized by the presence of cells expressing IFN-gamma (about 25% of hFCs) and CXCR4 (about 31% of hFCs) (FIG. 1B). In addition, about 65% of hFCs resemble tolerogenic plasmacytoid dendritic cells (B220+/CD11c+/CD11b−), and hFCs are capable of inducing antigen-specific $T_{reg}$ cells. Further, hFCs can be characterized by the presence, in lower levels, of markers such as, without limitation, CD16, CD52, NKp30, NKp44, NKp46, CD162, CD11a and CD62L.

Figure 2:
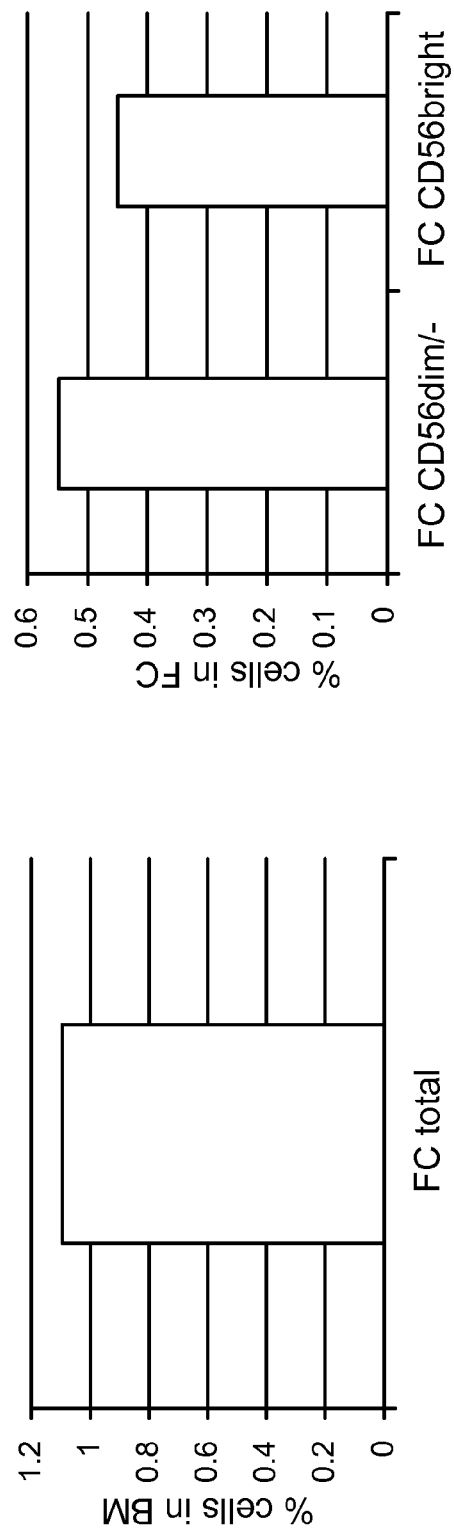
FIG. 2 is a graph showing the CD56$^{dim/neg}$ and CD56$^{bright}$ sub-populations within CD8+/alpha beta TCR− hFCs.

Within the population of CD8+/alpha beta TCR− hFCs, there are two subpopulations: CD8+/alpha beta TCR−/CD56$^{dim/neg}$ (about 55% of hFCs) and CD8+/alpha beta TCR−/CD56$^{bright}$ (about 45% of hFCs) (FIG. 2). As is understood by those skilled in this art, CD56$^{dim/neg}$ cells refer to a population of cells that express a relatively small amount of CD56 (CD56$^{dim}$) and cells that do not express CD56 (CD56$^{neg}$); while CD56$^{bright}$ cells refer to cells that express a relatively large amount of CD56 (CD56$^{bright}$).

Figure 3A:
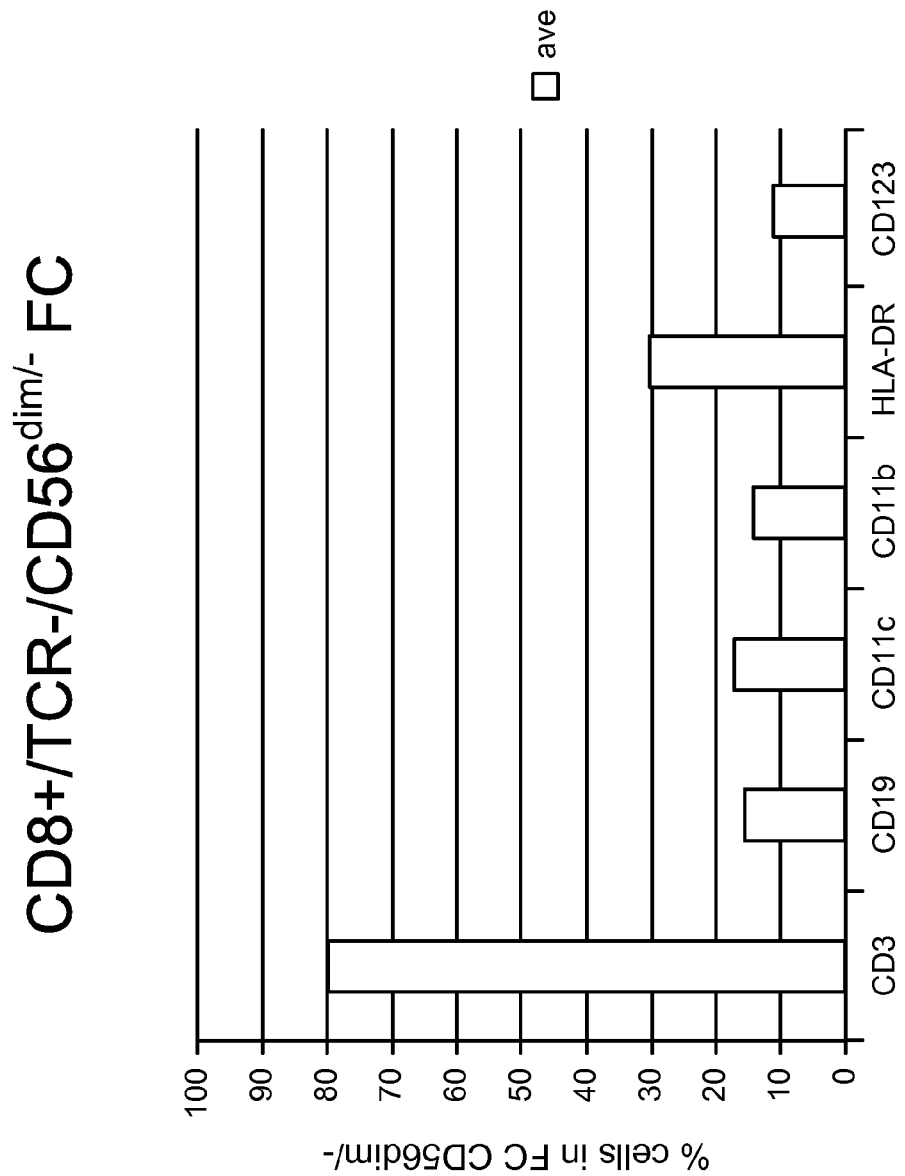
FIG. 3A is a graph showing representative phenotypic analysis of the CD8+/alpha beta TCR−/CD56$^{dim/neg}$ hFC sub-population.
Figure 3B:
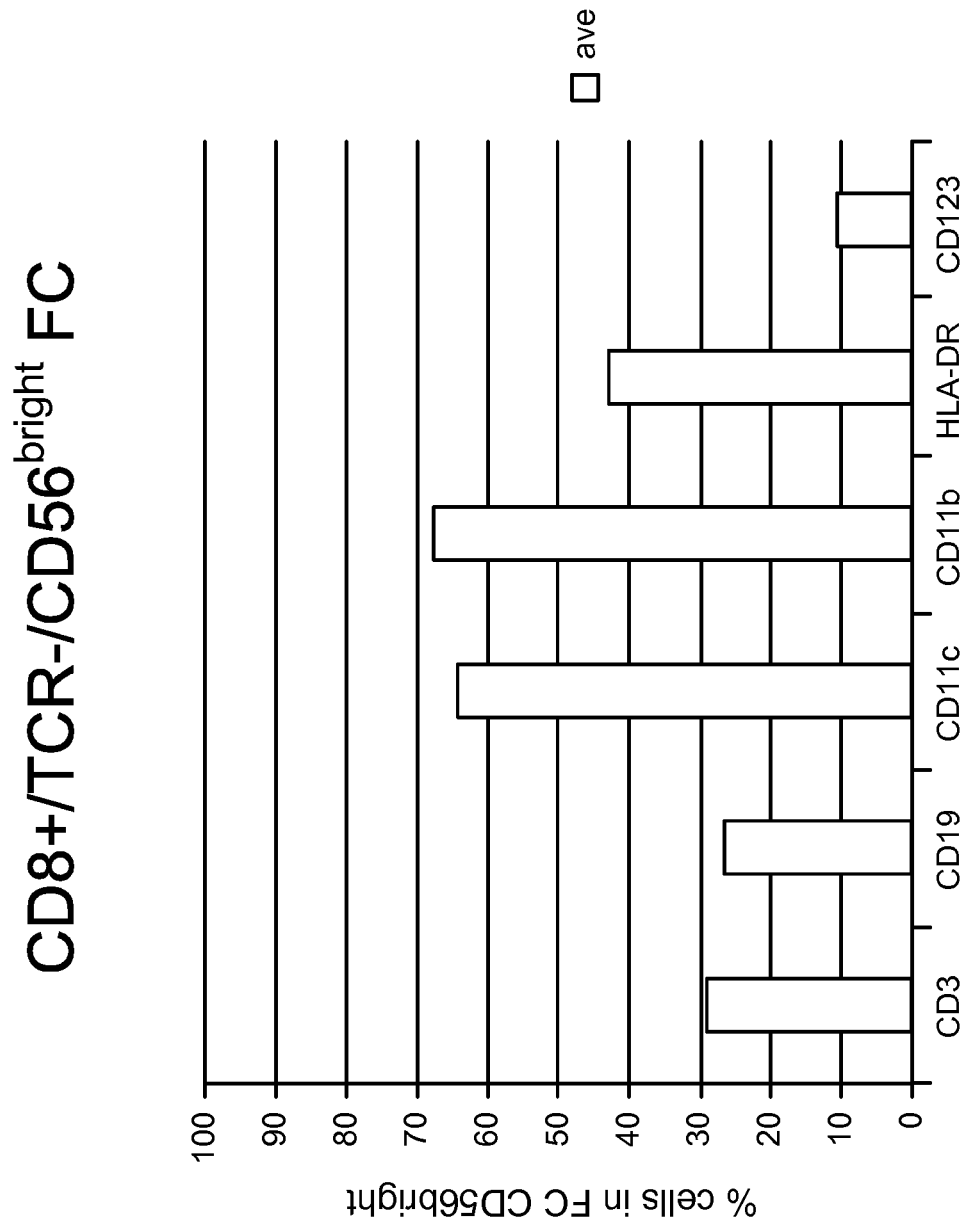
FIG. 3B is a graph showing representative phenotypic analysis of the CD8+/alpha beta TCR−/CD56$^{bright}$ hFC sub-population.

Within the CD8+/alpha beta TCR−/CD56$^{dim/neg}$ sub-population of hFCs, the majority of cells express CD3 epsilon (about 80%), approximately a third of the cells express HLA-DR (about 30%), and a lower percentage of cells express CD11c (about 17%), CD19 (about 16%), CD11b (about 14%), and CD123 (about 11%) (FIG. 3A). Thus, the majority of cells within the CD8+/alpha beta TCR−/CD56$^{dim/neg}$ hFC sub-population are CD3 epsilon+/CD19−. Within the CD8+/alpha beta TCR−/CD56$^{bright}$ sub-population of hFCs, approximately 65% of cells express CD11c, about 67% of the cells express CD11b, and about 40% of the cells express HLA-DR, while CD3 epsilon, CD19, and CD123 are expressed at much lower levels (about 29%, about 25%, and about 10%, respectively) in this sub-population (FIG. 3B).

Thus, the majority of cells within the CD8+/alpha beta TCR−/CD56$^{bright}$ hFC sub-population are CD3 epsilon−/CD19+.

hFCs can be obtained from bone marrow, or any other physiologic source of hematopoietic cells such as, without limitation, the spleen, thymus, blood, embryonic yolk sac, or fetal liver. In one embodiment, hFCs are obtained from mobilized peripheral blood (in the presence of, for example, granulocyte colony-stimulating factor (G-CSF) or granulocyte-macrophage colony stimulating factor (GM-CSF). In another embodiment, hFCs are obtained from vertebral bone marrow.

Once hematopoietic cells are obtained, hFCs can be enriched, purified (or substantially purified) by various methods that typically use antibodies that specifically bind particular markers to select those cells possessing (or lacking) those particular markers. Cell separation techniques include, for example, cell sorting using a fluorescence activated cell sorter (FACS) and specific fluorochromes; biotin-avidin or biotin-streptavidin separations using biotin conjugated to cell surface marker-specific antibodies and avidin or streptavidin bound to a solid support (e.g., affinity column matrix or a plastic surface); magnetic separations using antibody-coated magnetic beads; or destructive separations such as antibody and complement or antibody bound to cytotoxins or radioactive isotopes. Methods of making antibodies that can be used in cell separations are well known in the art. See, for example, U.S. Pat. No. 6,013,519.

Separation using antibodies directed toward specific markers can be based upon negative or positive selections. In separations based on negative selection, antibodies that are specific for markers that are present on undesired cells (non-hFCs) and that are not present on the desired cells (hFCs) are used. Those (undesired) cells bound by the antibody are removed or lysed and the unbound cells retained. In separations based on positive selection, antibodies that are specific for markers that are present on the desired cells (hFCs) are used. Those cells bound by the antibody are retained. It will be understood that positive and negative selection separations may be used concurrently or sequentially. It will also be understood that the present disclosure encompasses any separation technique that can be used to enrich or purify the hFCs described herein.

One well-known technique for antibody-based separation is cell sorting using, for example, a FACS. Briefly, a suspended mixture of hematopoietic cells are centrifuged and resuspended in media. Antibodies that are conjugated to fluorochromes are added to allow the binding of the antibodies to the specific cell surface markers. The cell mixture is then washed and run through a FACS, which separates the cells based on their fluorescence, which is dictated by the specific antibody-marker binding. Separation techniques other than cell sorting additionally or alternatively can be used to obtain hFCs. One such method is biotin-avidin (or streptavidin)-based separation using affinity chromatography. Typically, such a technique is performed by incubating hematopoietic cells with biotin-coupled antibodies that bind to specific markers, followed by passage of the cells through an avidin column. Biotin-antibody-cell complexes bind to the column via the biotin-avidin interaction, while non-complexed cells pass through. The column-bound cells can be released by perturbation or other known methods. The specificity of the biotin-avidin system is well-suited for rapid separation.

Cell sorting and biotin-avidin techniques provide highly specific means for cell separation. If desired, less specific separations can be utilized to remove portions of non-hFCs from the hematopoietic cell source. For example, magnetic bead separations can be used to initially remove non-facilitating differentiated hematopoietic cell populations including, but not limited to, T-cells, B-cells, natural killer (NK) cells, and macrophages (MAC) as well as minor cell populations including megakaryocytes, mast cells, eosinophils, and basophils. In addition, cells can be separated using density-gradient separation. Briefly, hematopoietic cells can be placed in a density gradient prepared with, for example, Ficoll or Percoll or Eurocollins media. The separation can then be performed by centrifugation or automatically with, for example, a Cobel & Cell Separator '2991 (Cobev, Lakewood, Colo.). Additional separation procedures may be desirable depending on the source of the hematopoietic cell mixture and its content. For example, if blood is used as a source of hematopoietic cells, it may be desirable to lyse red blood cells prior to the separation of any fraction.

Although separations based on specific markers are disclosed, it will be understood that the present disclosure encompasses any separation technique(s) that result in a cellular composition that is enriched for hFCs, whether that separation is a negative separation, a positive separation, or a combination of negative and positive separations, and whether that separation uses cell sorting or some other technique, such as, for example, antibody plus complement treatment, column separations, panning, biotin-avidin technology, density gradient centrifugation, or other techniques known to those skilled in the art. Most sources of hematopoietic cells naturally contain about 0.5% to about 8% (e.g., typically about 1%) hFCs. The separations such as those disclosed herein can yield cellular compositions that are enriched for hFCs (i.e., include a greater number of hFCs than are found naturally in physiological hematopoietic cell sources). For example, cellular compositions are provided in which at least about 5% (e.g., at least about 8%, 10%, 12%, 15%, 20% or more) of the cells are hFCs as described herein. These compositions are referred to as "enriched" for hFCs. In another example, cellular composition are provided in which at least about 30% (e.g., at least about 35%, 40%, 50% or more) of the cells are hFCs as described herein. The compositions are referred to as "purified" for hFCs. Further processing, by either or both positive or negative selections, can yield cellular compositions in which at least about 60% of the cells (e.g., at least about 70%, 75%, 80%, 85%, 90%, 95%, or 99%) are hFCs as described herein.

Exemplary methods of obtaining cellular compositions that include hFCs are described herein. Those skilled in this art would understand that the examples described herein can be modified in a number of ways to still obtain hFCs or to obtain different amounts of hFCs. In the following examples, bone marrow is the source of hematopoietic stem cells. Bone marrow can be harvested (e.g., from a donor) by various methods well known to those skilled in the art. For example, bone marrow can be harvested from the long bones (e.g., femora or tibia), but also can be obtained from other bone cavities or the spine.

In one exemplary method, non-hFCs and non-HSCs can be removed from the bone marrow using one or more negative selections described herein. For example, T cells, also known as graft vs. host disease (GVHD)-producing cells, can be specifically removed from the cellular composition using antibodies directed toward T cell-specific markers such as alpha beta TCR+. In certain embodiments, an antibody directed toward delta gamma TCR+ can be used to remove a further subset of T cells. The resulting cellular composition is enriched for hFCs and HSCs, and also will contain other immature progenitor cells such as immature lymphoid and myeloid progenitor cells.

In another exemplary method, hFCs can be obtained from the bone marrow using one or more positive selections described herein. For example, hFCs can be purified by cell sorting (e.g., using FACS) with one or more of the markers described herein (e.g., CD8+, CD19, CD56).

In certain instances (e.g., non-therapeutic), it may be desirable to remove the HSCs from the cellular composition. HSCs can be removed from bone marrow using, for example, antibodies that bind CD34+ and, optionally, CD45+. See, for example, U.S. Pat. No. 5,061,620 or the LC Laboratory Cell Separation System, CD34 Kit (CellPro, Inc., Bothell, Wash.).

Methods of Using HFCs and Cellular Compositions Containing HFCs

The ability of hFCs to enhance engraftment of donor bone marrow cells in a recipient indicates that hFCs are useful in facilitating various therapy protocols. Using a cellular composition that is enriched for hFCs (e.g., contains about 5% to about 12% hFCs) significantly improves durable engraftment and eliminates graft vs. host disease (GVHD). Although not bound by any particular mechanism, it is believed that, once administered, the hFCs home to various hematopoietic cell sites in the recipient's body, including bone cavity, spleen, fetal or adult liver, and thymus. The hFCs become seeded at the proper sites, engraft, and begin establishing a chimeric immune system. It is possible that both the stem cells and the hFCs complex together to seed the appropriate site for engraftment.

Methods of administering a therapeutic cellular composition comprising hFCs to a recipient also are described herein. A therapeutic cellular composition as used herein refers to a composition that includes hFCs and HSCs. Such a composition can be produced using any of the methods described herein (e.g., positive and/or negative selections). A therapeutic cellular composition for administration to a recipient may include a total of between about $1 \times 10^8$ cells and $3 \times 10^8$ cells per kilogram of dosing weight of the recipient. Within a therapeutic cellular composition, the number of HSCs can be between about $1 \times 10^5$ and $18 \times 10^6$ HSCs per kg of recipient dosing weight, and a similar range of hFCs can be administered. The exact numbers of cells that are used, however, will depend on many factors, including the number of cells in the original source of hematopoietic stem cells, the number of cells (e.g., hFCs and/or HSC) present after processing (e.g., enrichment and/or purification), as well as the condition of the recipient's health.

As described herein, obtaining hFCs typically involves depleting the alpha beta TCR+ T cells, as these are considered GVHD-producing cells. Therapeutically, however, the presence of alpha beta TCR+ T cells has been found to be beneficial in the cellular composition of HSCs and hFCs. As shown in the Example section herein, a cellular composition that includes alpha beta TCR+ T cells at a level that is greater than is generally considered to be therapeutic surprisingly promoted chimerism and engraftment. It is generally accepted that about $1 \times 10^5$ alpha beta TCR+ T cells/kg of recipient body weight is considered a lethal amount of T cells. However, in the methods described herein, amounts greater than that were routinely administered to recipients without adverse effects. Specifically, amounts between about $2.0 \times 10^6$ and $5.0 \times 10^6$ alpha beta TCR+ T cells (e.g., between about $2.5 \times 10^6$ and $4.5 \times 10^6$ alpha beta TCR+ T cells/kg recipient body weight; between about $3.0 \times 10^6$ and $4.0 \times 10^6$ alpha beta TCR+ T cells/kg recipient body weight; about $3.0 \times 10^6$ and $4.2 \times 10^6$ alpha beta TCR+ T cells/kg recipient body weight; about $3.2 \times 10^6$ alpha beta TCR+T cells/kg recipient body weight; or about $3.8 \times 10^6$ alpha beta TCR+ T cells/kg recipient body weight) can be included in a therapeutic cellular composition.

Accordingly, depending on the procedures and methods used to obtain the HSC and hFC therapeutic cellular composition, the number of alpha beta TCR+ T cells in the composition may need to be adjusted. For example, in certain embodiments, alpha beta TCR+ T cells can be added back to the T cell-depleted HSC and hFC composition in order to obtain the desired number. In other embodiments, the depletion step can be modified so that only the desired about of T cells are depleted, thereby leaving the desired amount of T cells in the composition. In order to achieve the desired amount of T cells in a therapeutic cellular composition, the number of T cells can be determined, for example, prior to depletion (e.g., in the starting material) or following the depletion step. Methods of determining the number of cells (e.g., T cells) in a sample are well known in the art (e.g., FACS).

Therapeutic cellular compositions generally are administered intravenously, but other modes of administration such as direct bone injection can be used. The therapeutic cellular compositions described herein, even in the presence of higher-thantherapeutic levels of alpha beta TCR+ T cells, result in durable chimerism. As used herein, durable chimerism refers to a recipient's immune system that is at least about 1% (e.g., at least about 2%, 3%, 4%, 5%, 6%, 7%, 8%, 9%, 10%, 25%, 50%, 75% or more (e.g., 100%)) donor origin for greater than 6-months post-transplant (e.g., 1-year or more post-transplant). In addition, durable chimerism can be achieved using the therapeutic cellular composition described herein even in recipients who are not HLA-matched to their donor or who are only partially matched with their donor. Accordingly, the therapeutic cellular compositions described herein allow for transplantation between a donor and a recipient that are syngeneic to one another and should allow for transplantation between a donor and a recipient that are allogeneic to one another.

Traditionally, methods of establishing a chimeric immune system required destroying the immune system of the recipient, which results in ablation of the recipient's HSCs. This may be accomplished by techniques well known to those skilled in the art and include, without limitation, irradiating the recipient with selected levels of total body irradiation, administering specific toxins or chemotherapeutic agents to the recipient, administering specific monoclonal antibodies or monoclonal antibodies attached to toxins or radioactive isotopes to the recipient, or combinations thereof. Notably, administering the hFCs described herein (e.g., in the therapeutic cellular composition) to a recipient significantly reduces the amount conditioning required of a recipient for successful engraftment and also significantly reduces the amount of immunosuppression required following transplantation. For example, destroying a recipient's immune system often involves lethally irradiating the recipient with 950 centigray (cGy) of total body irradiation (TBI), while the procedures described herein utilize a conditioning regimen with as little as 25 cGy to 200 cGy of TBI.

The ability to establish successful chimerism allows for significantly improved survival following transplant. The present disclosure provides for methods of transplanting a donor physiological component, such as, for example, organs, tissue, or cells. Using the hFCs in the methods disclosed herein results in a recipient who has a chimeric immune system, which is completely immunotolerant to transplanted donor organ, tissue, or cells, but competently rejects third party grafts. Transplanted donor organ, tissue, or cells are able to perform their respective functions in the recipient. For example, transplanted islet cells can provide an effective treatment for diabetes. In addition, permanent acceptance of endocrine tissue grafts (thyroid, parathyroid, adrenal cortex, adrenal medulla, islets) as well as kidney, liver, heart, and composite tissues such as face, hand and other extremities has been demonstrated. It will be understood that a mixed chimeric immune system can be produced in a recipient before, during, or after transplantation of an organ, tissue or cells, but typically is produced before or at the same time as the transplantation.

The use of hFCs in establishing a chimeric immune system can significantly expand the scope of diseases that can be treated using bone marrow transplantation. Beyond transplantation (e.g., heart, kidney, liver, pancreatic islets, and hand or face), the ability to establish a successful chimeric hematopoietic system in a recipient can be used to treat other diseases or disorders that are not currently treated by bone marrow transplantation because of the morbidity and mortality associated with GHVD. Autoimmune diseases involve attack of an organ or tissue by one's own immune system. However, when a chimeric immune system is established, the body can relearn what is foreign and what is self. Establishing a chimeric immune system using the hFCs described herein can reduce or halt the autoimmune attack causing the condition. Autoimmune diseases that can be treated using the hFCs described herein include, for example, type I diabetes, systemic lupus erythematosus, multiple sclerosis, rheumatoid arthritis, psoriasis, or Crohn's colitis.

It may also be possible to treat Alzheimer's disease using the cellular compositions described herein. The cellular compositions disclosed herein also can be used to treat hemoglobinopathies such as, for example, sickle cell anemia, spherocytosis or thalassemia, as well as metabolic disorders such as Hunters disease, Hurlers disease, chronic granulomatous disease, leukodystrophy, and enzyme defects. In addition, the cellular compositions described herein can be used to treat leukemias or other rare childhood disorders (e.g., ADA deficiency, aplastic anemia or SCID), or the cellular compositions described herein can be used in regenerative repair (e.g., macular degeneration, myocardial infarction, or islet regeneration).

In accordance with the present disclosure, there may be employed conventional molecular biology, cell biology, microbiology and biochemical techniques within the skill of the art. Such techniques are explained fully in the literature. The methods and compositions will be further described in the following examples, which do not limit the scope of the methods and compositions described in the claims.

EXAMPLES

Section A—Colony Forming Cell Assays

Example 1

Purification of HSC and hFC

HSC and hFC were isolated from Human Vertebral Bone Marrow (VBM) or Mobilized Peripheral Blood (MPB) by multiparameter, live sterile cell sorting (FACSVantage SE: Becton Dickinson). Briefly, VBM or MPB was stained with directly labeled monoclonal antibodies (mAbs) at saturating concentrations for 30 min. HSCs: CD34+/CD45+; and hFCs: CD8+/TCR−/CD56$^{dim/neg}$. Both cell populations were sorted and analyzed for purity. Only 85% or greater purity levels were accepted.

Example 2

HSC and hFC Sorting and Enumeration

HSCs were sorted and enumerated based on the ISHAGE protocol. See, Sutherland et al., 1996, "The ISHAGE guidelines for CD34+ cell determination by flow cytometry," *J. Hematotherapy*, 5:213-26. Briefly, CD45-FITC/CD34-PE combination parameters provided a clinically relevant reflection of the peripheral blood stem/progenitor cell compartment. Plot 1 was formatted with Forward Scatter (FSC; x-axis) vs Side Scatter (SSC; y-axis), and a region (R1) was drawn around the lymphocyte, monocyte and granulocyte populations excluding debris. From R1, Plot 2 was formatted with CD45 FITC versus Side Scatter, and R1 was drawn so that CD45-events were excluded. From R2, Plot 3 was formatted with CD34 PE versus Side Scatter, and R3 was drawn only around the CD34+ population. From R3, Plot 4 was formatted with CD45-FITC versus SSC of CD34+ cells. Cells forming a cluster with characteristic low SSC and low to intermediate CD45 fluorescence were gated and designated R4. Nonspecific stained events were excluded from this region. From R4, Plot 5 was formatted with FSC (x-axis) versus SSC (y-axis). A cluster of events meeting all the fluorescence and light scatter criteria of CD34+ stem/progenitor cells appeared in Plot 5.

Figure 4:
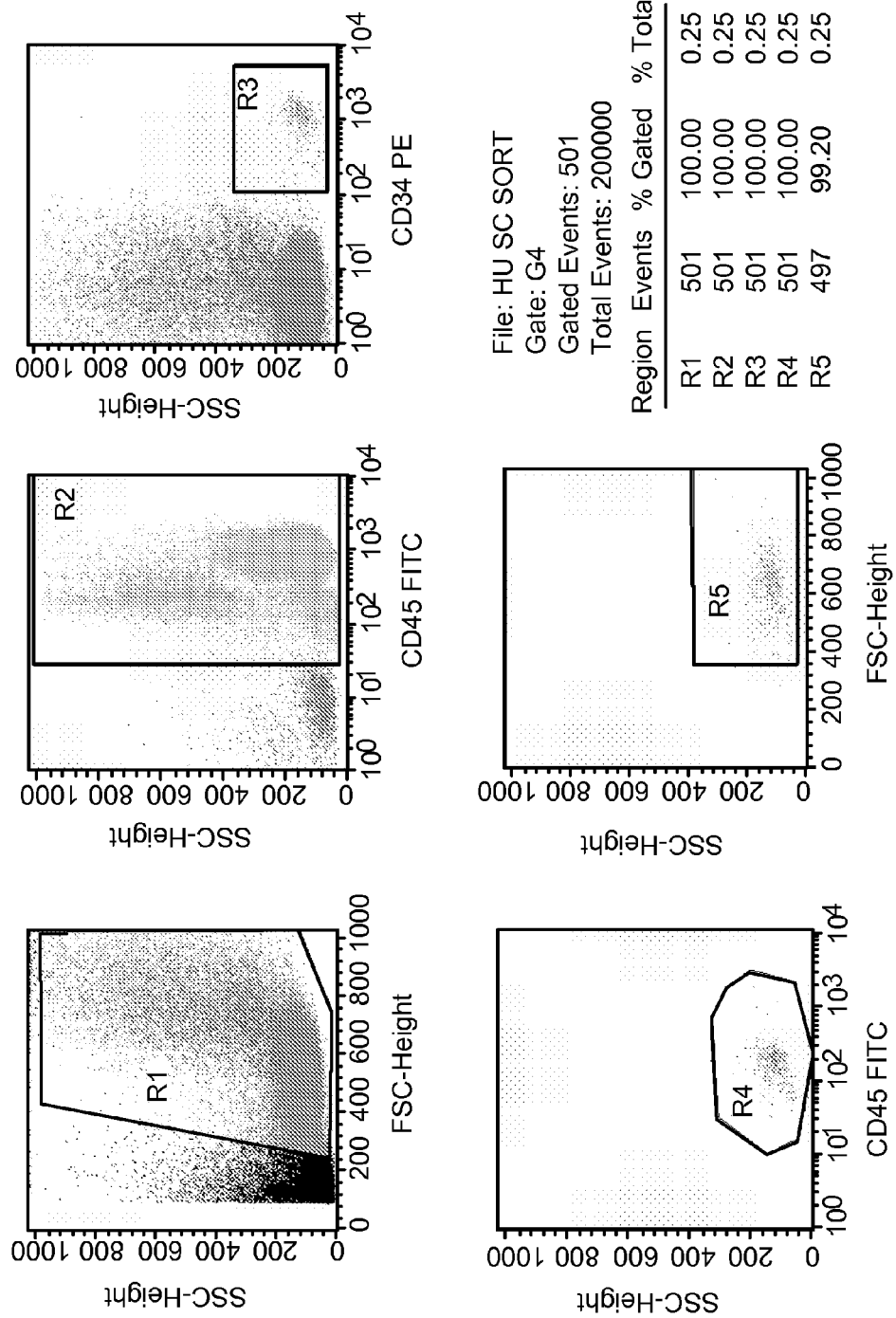
FIG. 4 shows the gating strategy for sorting and enumeration of human HSCs.
Figure 5:
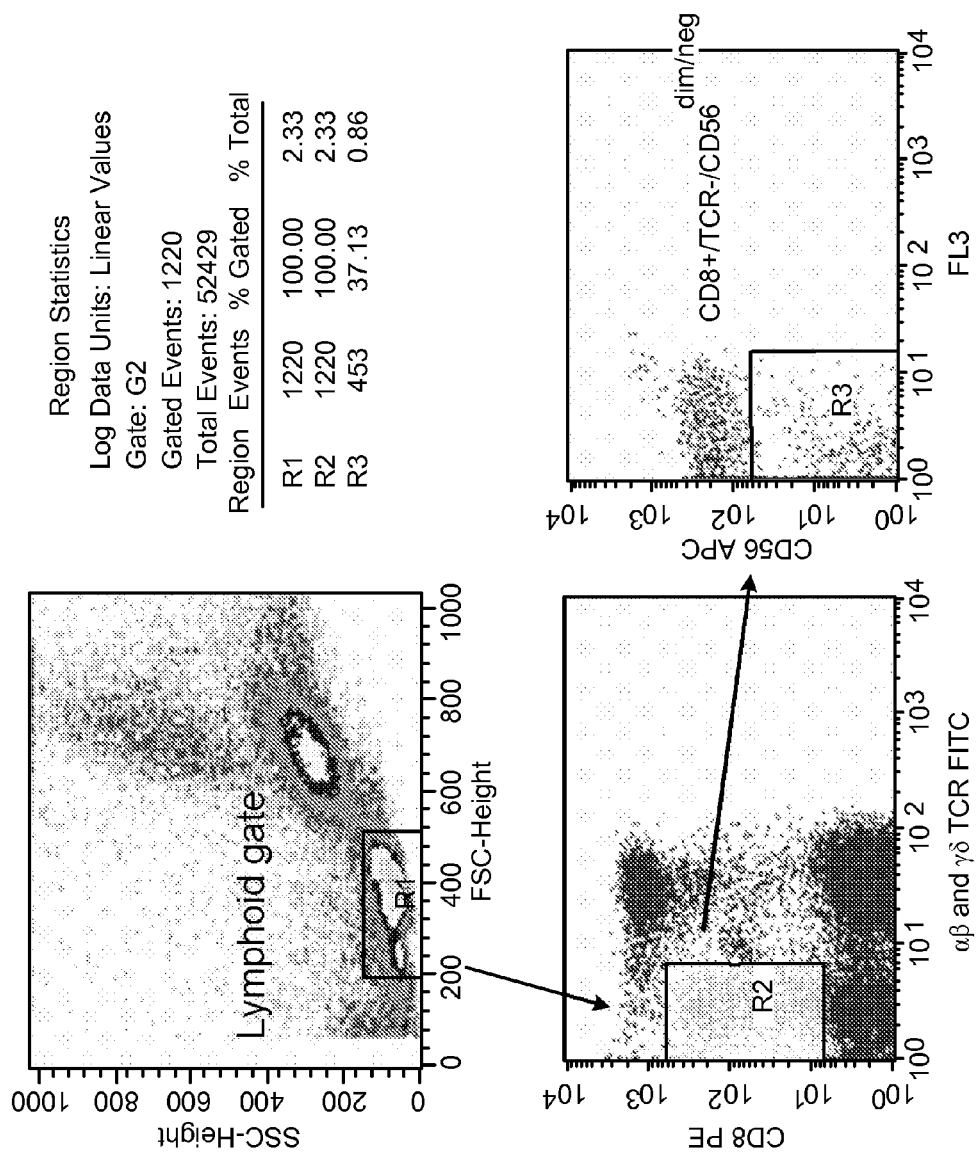
FIG. 5 shows the gating strategy for sorting and enumerating human hFCs.

FIG. 4 shows the gating strategy for the sorting and enumeration of human HSCs using the ISHAGE protocol. FIG. 5 shows the gating strategy for the sorting and enumeration of human hFCs.

Example 3

Colony-Forming Cell Assay with hFCs

Following cell sorting, HSCs (CD45+/CD34+) alone or HSCs and hFCs (CD45+/CD34+ plus CD8+/TCR−/CD56$^{dim/neg}$) or HSCs+ T cells as a control were either immediately plated in methylcellulose (0 hr) or pre-incubated for 18 hrs in cell culture media before plating in methylcellulose. All cell samples were cultured in quadruplicate. After 14 days of culturing at 37° C. and 5% $CO_2$, colonies containing more than 50 cells were scored.

Without pre-incubation, there was no significant difference in colonies generated by HSC alone vs. HSC plus hFC. Strikingly, when HSCs were co-incubated with hFCs for 18 hrs prior to placement in the CFC assay, hFC significantly ($p<0.005$) enhanced colony formation compared to HSC alone and HSC co-incubated with CD8+ T cells. These results indicate that human hFCs, like mouse hFCs, exert a protective effect on HSCs and promote the generation of more primitive multipotent progenitors in vitro.

Example 4

Colony-Forming Cell Assay with a Sub-Population of hFCs

Colony Forming Culture (CFC) Assay: 15,000 HSCs were cultured with or without 30,000 CD8+/alpha beta TCR−/CD56$^{dim/neg}$ hFCs for 0 hrs or 18 hrs in culture media in a 96 well plate and incubated at 37° C. After culture, cells were resuspended in methylcellulose and used in a CFC Assay. Colonies were counted on day 14.

Summary and Results: To evaluate the function of CD8+/alpha beta TCR−/CD56$^{dim/neg}$ hFCs in vitro, HSCs were incubated with CD8+/alpha beta TCR−/CD56$^{dim/neg}$ hFCs for 18 hrs and then cultured in methylcellulose for 14 days in a colony-forming cell assay. HSC plus CD8+/alpha beta TCR−/CD56$^{dim/neg}$ hFCs generated significantly more colonies compared with HSCs alone ($p=0.0038$), demonstrating that CD8+/alpha beta TCR−/CD56$^{dim/neg}$ hFCs have a direct effect on the clonogenicity of HSCs.

Section B—Characterization of Human hFCs In Vivo

Example 1

Chimerism and Engraftment in a Mouse Model

It has been shown previously that CD8$^+$/TCR$^-$ hFCs enhance engraftment of purified HSCs in allogeneic and syngeneic mouse recipients (Fugier et al., 2005, *J. Exp. Med.*, 201(3):373-383). In addition, it has been shown in mice that hFCs enhance the clonogenicity and promote the generation of more primitive multipotent HSC progenitors in vitro (Rezzoug et al., 2008, *J. Immunology*, 180(1):49-57).

One goal was to achieve human HSC chimerism in a mouse model. Briefly, CD34$^+$, CD45$^+$ human HSCs were sorted from G-CSF mobilized peripheral blood, and 100,000 sorted human HSCs were transplanted into NOD/SCID/IL2 receptor (IL2R) γ chain$^{null}$ mice conditioned with 325 cGy TBI. Whole blood was collected from transplanted mice one month following transplantation, and PBL typing was performed using antibodies specific for human T cells, B cells, natural killer cells, dendritic cells, and monocytes. Results showed that an average of 3.2% human HSC chimerism was achieved following transplantation with 100,000 hHSCs.

Experiments then were performed in which 100,000 hHSCs alone or 100,000 hHSCs+300,000 hFCs were transplanted into NOD/SCID/IL2Rγ$^{null}$ mice conditioned with 325 cGy TBI. Multilineage PBL typing was performed at 30 days after transplantation as described above.

The results of these experiments demonstrated that the HSC+hFC group produced a higher percentage of human T cells (CD4, CD8, DC; see Table 1) and human monocytes (CD33; Table 2) compared to the HSC alone group. The percentage of donor chimerism in lymphoid gate and myeloid gate are summarized in Table 3.

TABLE 1

Percentage of human T cells, NK cells, B cells, and DCs in lymphoid gate

| Group | Mouse | CD8 | CD4 | CD3 | αβ/δγ TCR | NK CD56 | B cell CD19 | DC CD11c |
|---|---|---|---|---|---|---|---|---|
| HSC alone | A | 0 | 0.1 | 0.1 | 0.1 | 0.1 | 0.1 | 0 |
| | B | 0 | 0 | 0.1 | 0.3 | 0.2 | 0 | 0 |
| | C | 0 | 0 | 0 | 0.1 | 0 | 0 | 0 |
| HSC + hFC | D | 0.1 | 0.5 | 0.4 | 0.5 | 0.1 | 0.1 | 0.1 |
| | E | 0.1 | 0.1 | 0.1 | 0.1 | 0.1 | 0 | 0.1 |
| | F | 0 | 0.1 | 0.1 | 0.1 | 0.1 | 0.1 | 0.1 |

TABLE 2

Percentage of human DCs and monocytes in myeloid gate

| Group | Mouse | CD11c | CD33 |
|---|---|---|---|
| HSC alone | A | 4.8 | 9.2 |
| | B | 0.6 | 5 |
| | C | 0 | 0 |
| HSC + hFC | D | 3.2 | 6.6 |
| | E | 4.1 | 8.1 |
| | F | 8.2 | 14.9 |

TABLE 3

Percentage of human hematopoietic cells

| Group | Mouse | Lymphoid CD45 | Myeloid CD45 |
|---|---|---|---|
| HSC alone | A | 1.5 | 9.2 |
|  | B | 1.5 | 5.8 |
|  | C | 0.3 | 0.3 |
| HSC + hFC | D | 1.1 | 8.2 |
|  | E | 0.8 | 9.4 |
|  | F | 1.2 | 15.9 |

Example 2

Engraftment of CD8+/Alpha Beta TCR−/CD56$^{dim/neg}$ in a Mouse Model

Animals: Five to 6-week-old male non-obese diabetic (NOD)/SCID/interleukin-2 receptor (IL-2r) gamma-chain knockout (NSG) mice were purchased from the Jackson Laboratory (Bar Harbor, Me.).

Purification of HSCs and hFCs: HSCs and FCs were sorted from human G-CSF-mobilized peripheral blood by multiparamter, live sterile cell sorting (FACSVantage SE and FACSAria; Becton Dickinson, Mountain View, Calif.).

Phenotype of human CD8+/alpha beta TCR− hFCs: G-CSF mobilized PBMC were stained with anti-human CD8 alpha, alpha beta TCR, delta gamma TCR, CD56, CD3 epsilon, CD19, CD11c, CD11b, HLA-DR, Foxp3, INF-gamma, TGF-beta, CXCR4, and SDF-1 monoclonal antibodies, and analyzed by LSR using Cell Quest Software (Becton Dickinson).

HSC and FC transplantation: In the human HSC+FC xenogeneic model, 100,000 human HSCs with or without 300,000 sorted CD8+/alpha beta TCR−/CD56$^{dim/neg}$ hFCs were transplanted into NOD/SCID/IL-2r gamma$^{null}$ mice recipients conditioned with 325 cGy TBI.

Assessment of chimerism: Donor cell engraftment was evaluated in peripheral blood lymphocytes, bone marrow cells and splenocytes using 7-color flow cytometry.

Summary: To evaluate whether human CD8+/alpha beta TCR−/CD56$^{dim/net}$ hFCs enhance engraftment of human HSCs in vivo, 100,000 HSC alone or plus 300,000 CD8+/alpha beta TCR−/CD56$^{dim/net}$ hFCs was transplanted into NOD/SCID/IL2rg$^{null}$ (NSG) recipient mice conditioned with 325 cGy of total body irradiation. At 30 days after transplantation, 8 of 21 (38%) recipients of HSC alone engrafted. In contrast, 81% of recipients (n=16) receiving HSC plus CD8+/alpha beta TCR−/CD56$^{null/net}$ hFCs engrafted, and donor lymphocyte and donor monocyte chimerism in peripheral blood was 0.53%±0.16% and 3.93%±1.28%, respectively.

At 6 months after transplantation, NSG recipients of HSC alone lost donor chimerism in peripheral blood and little to no donor cells were detected in spleen and bone marrow. In contrast, NSG recipients of HSC+CD8+/alpha beta TCR−/CD56$^{dim/net}$ hFCs exhibited durable donor chimerism in peripheral blood and showed significantly higher levels of donor chimerism in spleen (about three-times as many donor lymphocytes and about twice as many donor monocytes) and bone marrow (about ten-times as many donor lymphocytes and about four-times as many donor monocytes) compared to recipients of HSC alone.

Section C—Treatment of Sickle Cell Disease (SCD) in Humans

Example 1

The Sickle Cell Disease (SCD) Preliminary Experiment

Two sickle-cell disease (SCD) patients were previously treated in a pilot experiment to try to establish mixed chimerism. Both SCD patients were at high risk for complications from their disease. Whether a combination of 200 cGy TBI with fludarabine, MMF, and CyA could establish engraftment in patients with SCD was evaluated. Only transient engraftment, however, was achieved. The conditioning was well tolerated, and no severe adverse events occurred; however, endogenous hematopoiesis reappeared.

To overcome the transfusion/sensitization barrier, improvements were made to the protocol. For example, Campath, which is a humanized anti-CD52 monoclonal antibody that is a powerful lytic agent for mature T cells, B cells and NK cells, was added to the clinical conditioning regimen. Two cycles of Campath were administered (month −2 and month −1) with the rationale that the first cycle would deplete mature B cells and cause homeostatic proliferation of memory B cells to replace the depleted B cells and the second cycle would deplete the proliferating memory B cells. It was hypothesized that the broad lymphoid specificity of Campath would provide a powerful approach to target T and B cells in the recipient that mediate the alloreactivity induced by transfusion therapy.

In one example, four doses of 10 mg/day of Campath-1H were administered at day −53 to −50, and another four doses of 7 mg/day of Campath-1H were administered at day −24 to −21. 30 mg/m$^2$ of Fludarabine was administered at day −5 to −3, and 200 cGy total body irradiation was administered at day −1 along with Mycophenolate mofetil and cyclosporine, which was continued until durable engraftment. FCs+HSCs were transplanted at day 0.

Figure 6A:
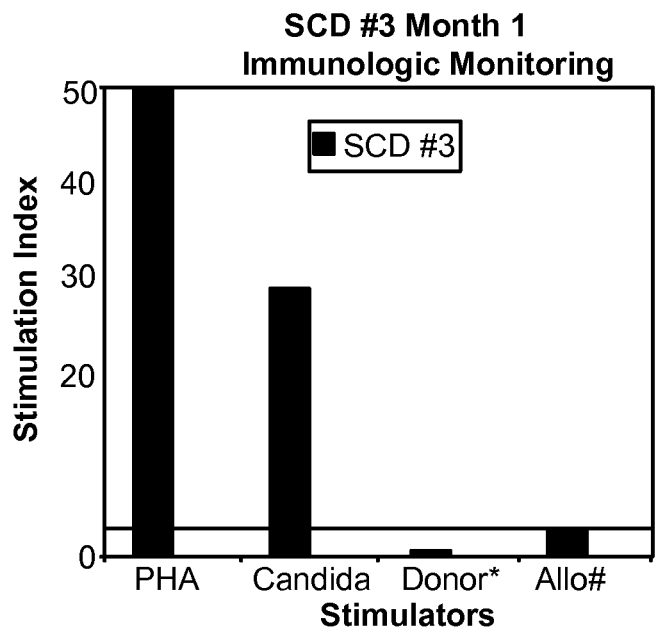
FIG. 6A is a graph showing the results of immunological monitoring in response to a number of stimulators 1-month post-transplantation in transplant patient SCD#3.
Figure 6B:
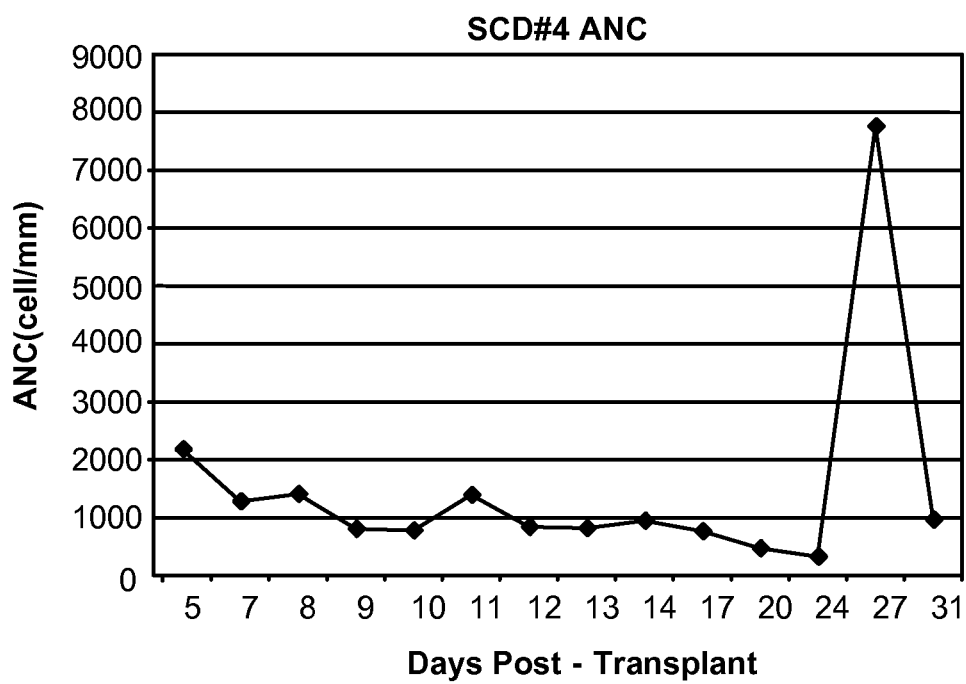
FIG. 6B is a graph showing the absolute neutrophil count (ANC) in transplant patient SCD#4.

Two subjects with SCD have been successfully transplanted under the revised protocol. Both subjects have maintained engraftment at 27 and 24 months post-transplant and are asymptomatic and transfusion independent. It was demonstrated that mixed chimerism can be established with minimal toxicity in sensitized recipients through partial recipient conditioning followed by transplantation with HSCs and hFCs to reduce the risk of GVHD while preserving engraftment. The reduced-intensity conditioning approach described herein is safe, well-tolerated and, in combination with the HSC+hFC graft, sufficient to induce stable mixed chimerism and dominantly normal RBC production in transfused patients Immunocompetence to respond to PHA, Candida, and alloantigen returned by 1 month post-transplant (FIG. 6A; a stimulation index of >3 is positive (horizontal line on graph)). The nadir occurred between day 9 and day 24 for both patients (absolute neutrophil count [ANC]<1,000) (FIG. 6B).

Example 2

SCD Patient #3—Transplanted in November 2005

SCD#3 (Date of Birth Nov. 2, 1998) is an African American female who experienced multiple pain crises and episodes of acute chest syndrome. She was maintained on transfusion therapy. Her HLA-identical sister with sickle cell trait served as her donor. The patient was conditioned with four doses of Campath-1H (30 mg/day) starting at day −53, and a second round of four doses of Campath-1H (30 mg/day) starting at day −24. She received 3 doses of fludarabine (30 mg/m² IV) starting at day −4, and then 200 cGy of TBI on day 0.

Figure 7A:
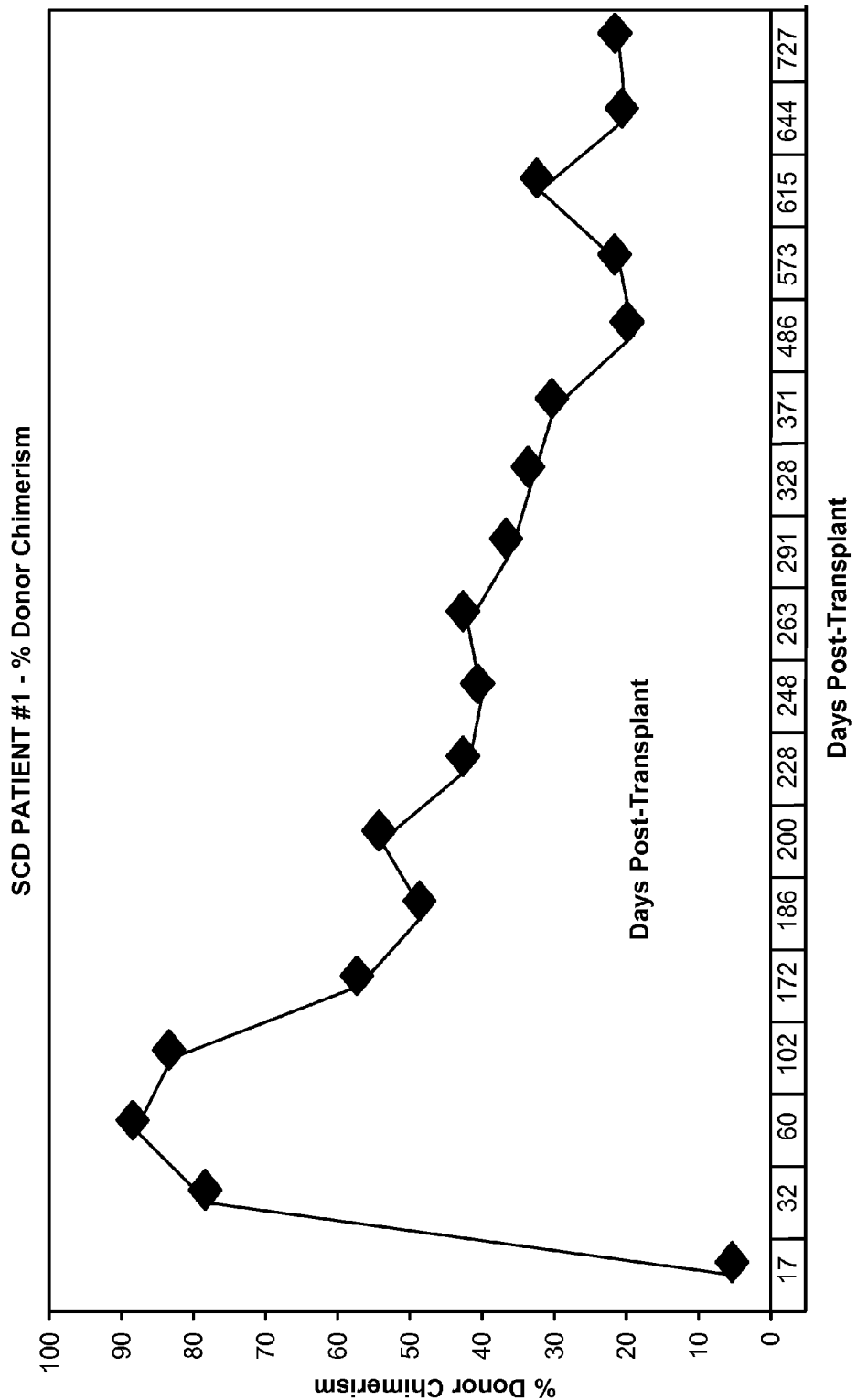
FIG. 7A is a graph showing the chimerism of transplant patient SCD#3.
Figure 7B:
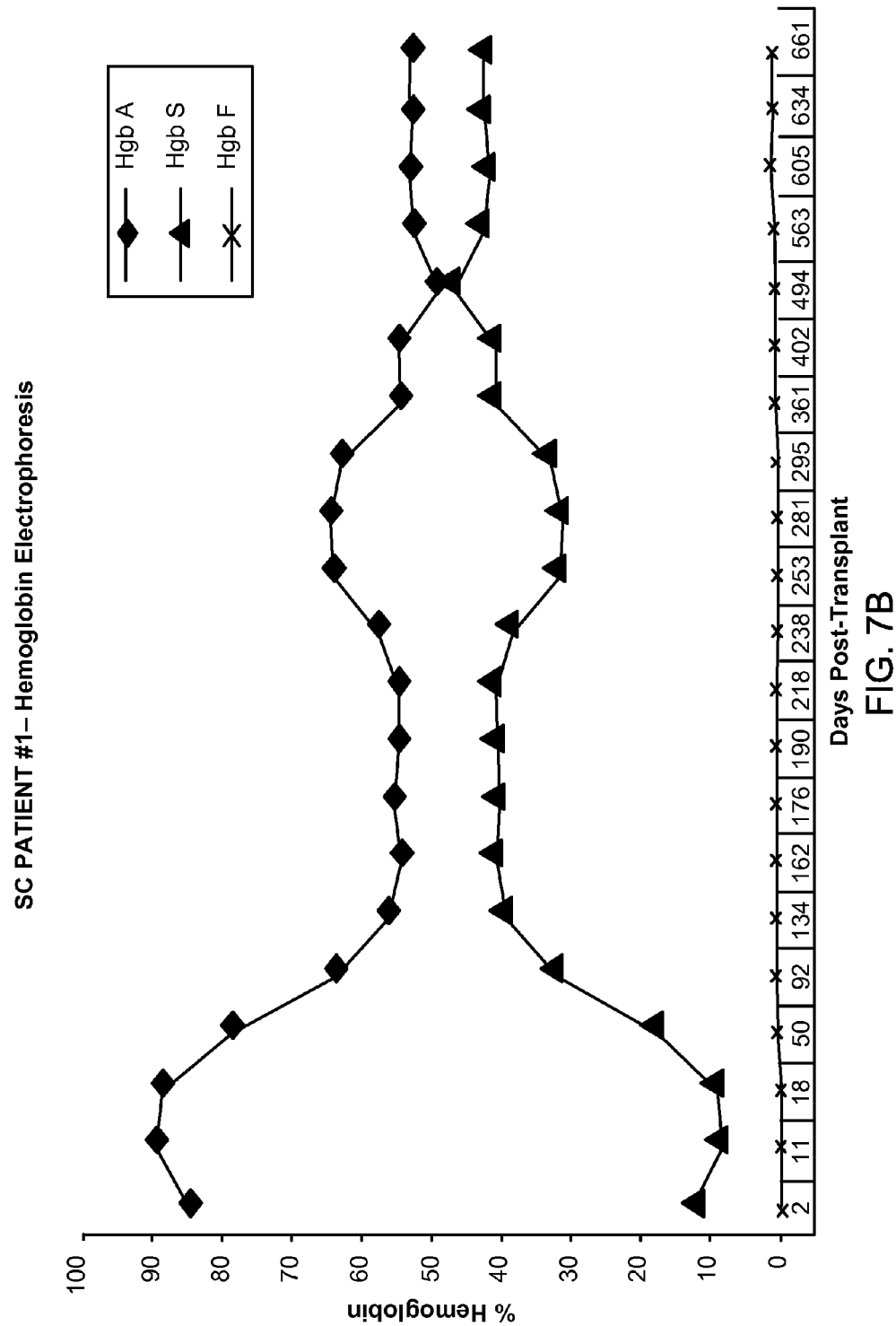
FIG. 7B is a graph showing the source of hemoglobin from the same transplant patient.

Post-transplant, she was treated with cyclosporine (1.5 mg/kg/bid) and MMF for 22 months. The immunosuppression was subsequently tapered and has been discontinued completely. The patient received $14.1 \times 10^6$ CD34+ cells/kg body weight, $43.5 \times 10^6$ alpha beta TCR cells/kg body weight and $5.4 \times 10^6$ hFCs/kg body weight. She showed 5% donor cell chimerism on Day 17 and 78% donor cell chimerism on day 32. She has been asymptomatic and has not required transfusions post transplant. At day 727 post-transplantation, she was 21% donor cell chimeric (FIG. 7A), and she had no evidence of GVHD. Although her total donor chimerism was approximately 30%, she was producing nearly 100% donor-derived trait RBC (FIG. 7B). At 1259 days post-transplantation, she produced 100% donor RBC and had T, B, and myeloid chimerism ranging between 10-30%. She was still transfusion independent and had not had any complications from her SCD.

During the processing procedure for SCD #3, some difficulty was experienced in recovering the correct fraction in the cell separation (Percoll) procedure due to the density of SCD trait marrow cells. Because the donor/recipient pair were HLA matched, the decision was made to abort the process and not deplete the product. Therefore, the patient received whole bone marrow. However, the efficacy of the conditioning was established in this candidate.

Example 3

SCD Patient #4—Transplanted in March 2006

Figure 8A:
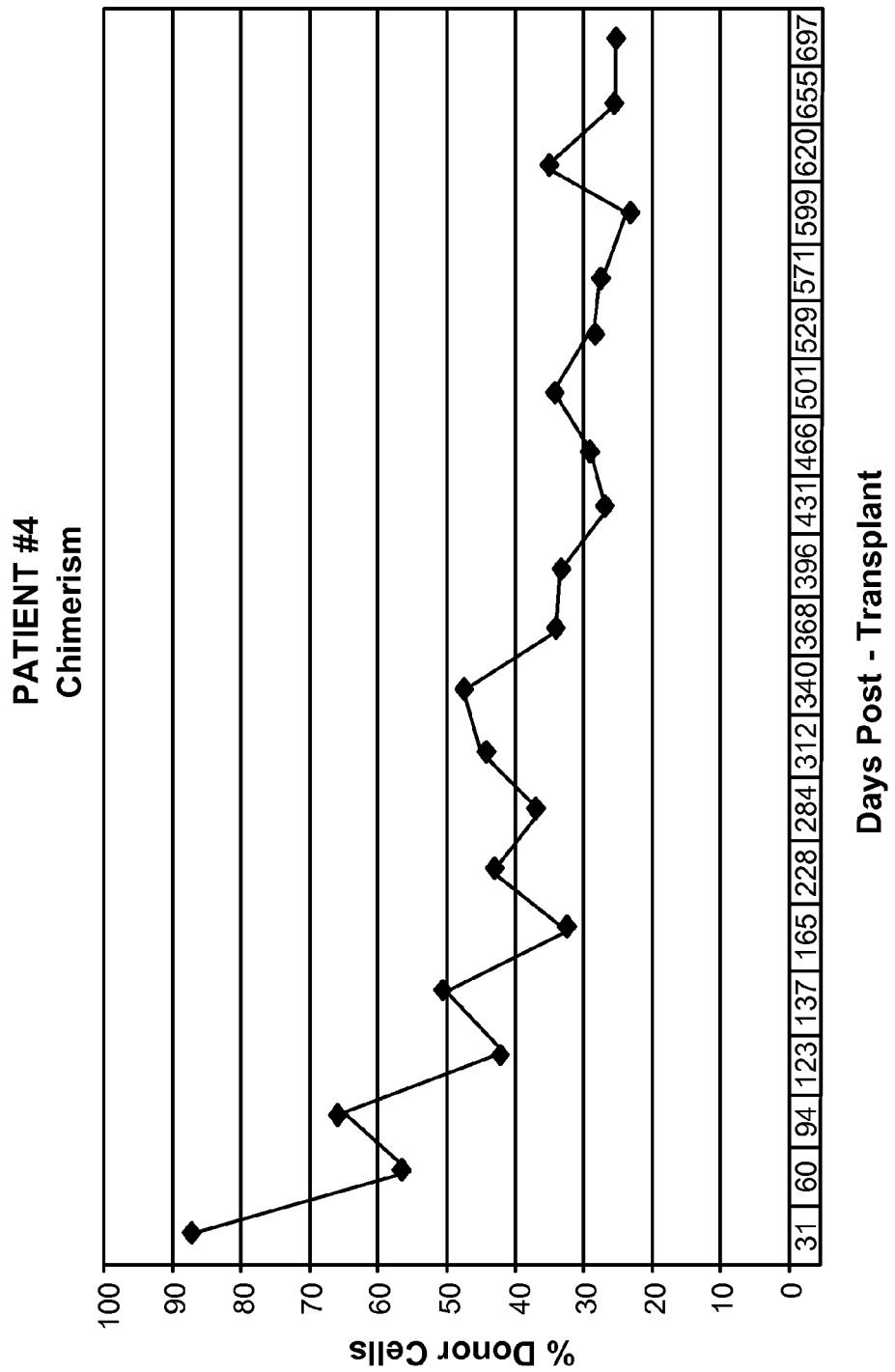
FIG. 8 are graphs showing the chimerism (Panel A), the source of hemoglobin (Panel B), and the reticulocyte counts (Panel C) for transplant patient SCD#4.
Figure 8B:
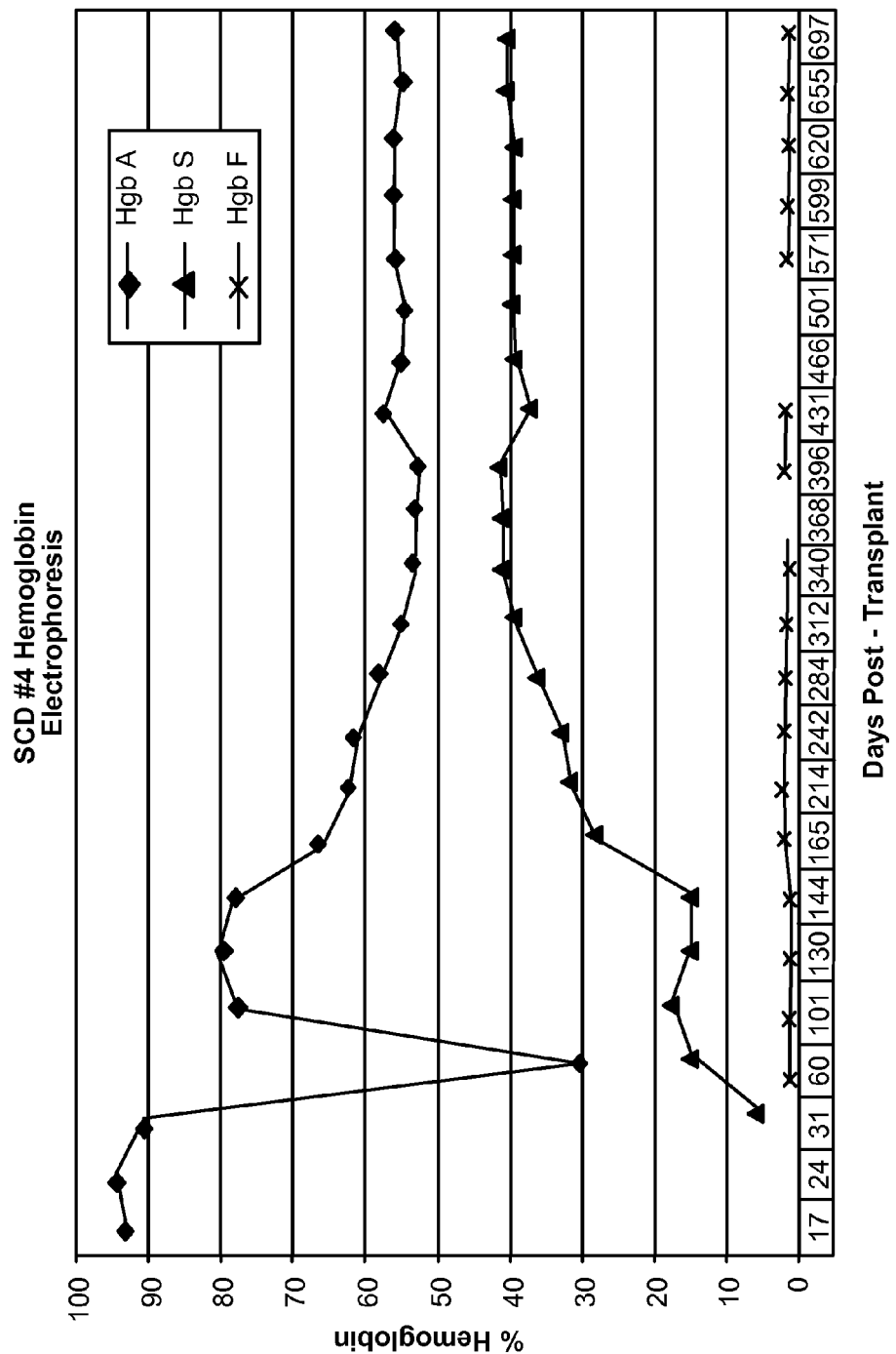
Figure 8C:
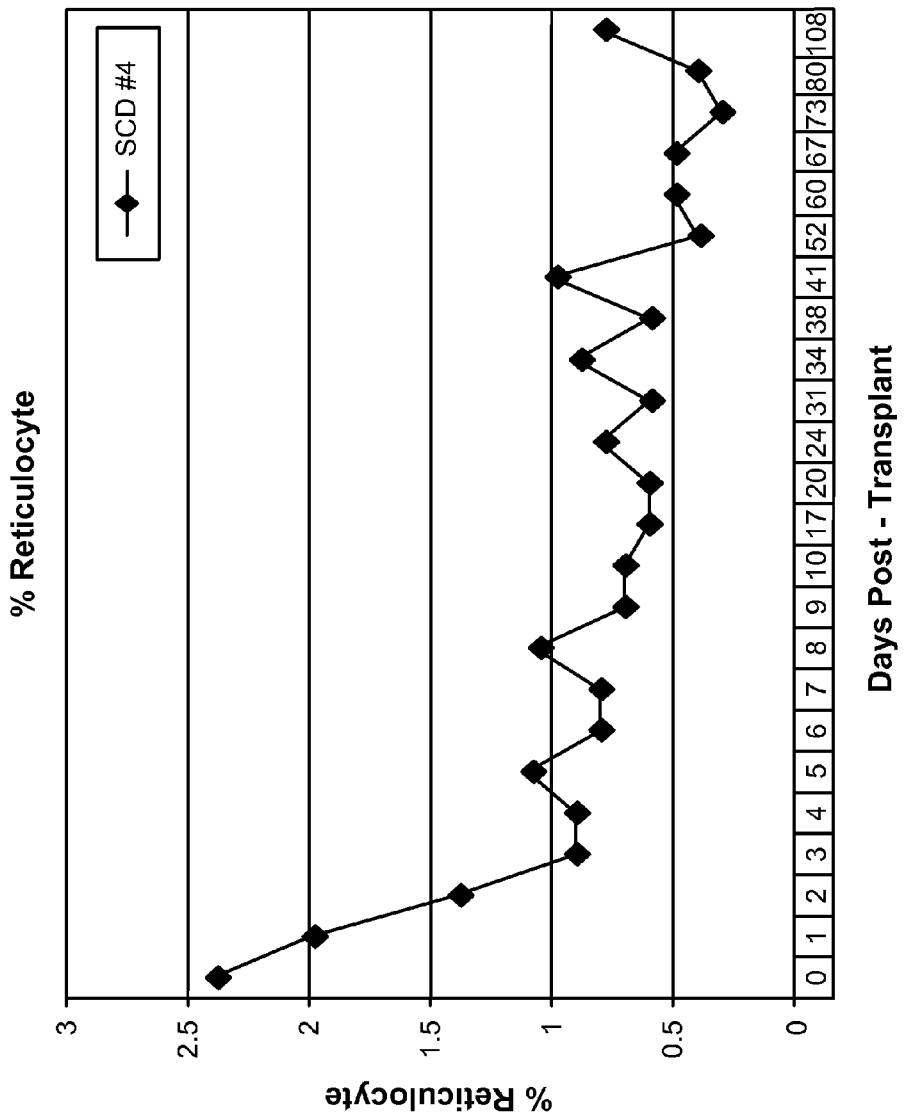

SCD#4 (Date of birth May 23, 1996) is a Nigerian male who suffered multiple pain crises and two acute chest syndromes prior to starting red cell exchange in 1999. The patient's HLA-identical sibling who had sickle cell trait served as his donor. The patient received the same non-myeloablative conditioning as SCD#3. His HSC+hFC dose was $5.24 \times 10^6$/kg CD34 cells, $0.55 \times 10^6$/kg c43-TCR cells and $0.35 \times 10^6$/kg hFC. He tolerated the conditioning very well and engrafted and chimeric (88% donor cells) at one month based on FISH. His donor chimerism was 28% as of day 697 (FIG. 8A). Donor T cell chimerism was 34% at day 501. The patient has remained asymptomatic since his transplant and is producing predominantly normal RBC (FIG. 8B). The reticulocyte counts for patient SCD#4 has ranged between 0.5% and 1%, which is within normal ranges (FIG. 8C).

Example 4

Summary

This section described successful transplantation of two heavily-transfused SCD patients using HLA-identical marrow from sibling donors. Both patients were successfully transplanted using reduced-intensity non-myeloablative conditioning and have remained disease free for >2 years. At enrollment, they were transfusion-dependent and at very high risk for painful crises and other complications. Both patients have been successfully weaned from immunosuppression.

Section D—Treatment of Sickle Cell Disease in Humans

Five individuals at high risk for morbidity and mortality from their thalassemia were enrolled on the protocol according to the inclusion and exclusion criteria below.

Example 1

Inclusion Criteria

The following criteria were established to identify individuals with thalassemia who have a high predicted morbidity and are at risk for early mortality: patients with alpha or beta thalassemia major; or patients with other complex and transfusion-dependent hemoglobinopathies. Individuals must also meet all of the following general inclusion criteria: individuals must have a related donor (identical or mismatched for 1, 2 or 3 HLA-A, -B or -DR loci); individuals must have adequate cardiopulmonary function as documented by echocardiogram or radionuclide scan (shortening fraction >26% or ejection fraction >40% or >80% of normal value for age); individuals must have adequate pulmonary function documented by FEV1 of >50% of predicted for age and/or DLCO (corrected for hemoglobin)>50% of predicted for age for patients >10 years of age (if patient cannot perform PFT's, resting pulse oximeter >85% on room air or clearance by the pediatric or adult pulmonologist is required); individuals must have adequate hepatic function as demonstrated by a serum albumin >3.0 mg/dL, and SGPT or SGOT <5 times the upper limit of normal; and individuals must have adequate renal function as demonstrated by a serum creatinine <2 mg/dL. If serum creatinine is >2 mg/dL, then a creatinine clearance test or nuclear medicine GFR should document GFR of ≥50 ml/min/1.73 m². There are no age limits for this protocol.

Example 2

Exclusion Criteria

Individuals are excluded from this trial if they meet any of the following criteria: the individual lacks related donors; the individual has uncontrolled infection or severe concomitant diseases, and may not tolerate reduced intensity transplantation; the individual exhibits severe impairment of functional performance as evidenced by a Karnofsky (patients >16 years old) or Lansky (children <16 years old) score of <70%; the individual exhibits renal insufficiency (GFR <50 ml/min/1.73 m²); the individual has a positive human immunodeficiency virus (HIV) antibody test result; the individual is pregnant as indicated by a positive serum HCG test; the individual's only donor is pregnant at the time of intended transplant; the individual is of childbearing potential and is not practicing adequate contraception; the individual has been exposed to previous radiation therapy that would preclude TBI; the individual is a Jehovah's witness; the individual has uncontrolled hypersplenism; or the individual exhibits severe alloimmunization with inability to guarantee a supply of adequate PRBC donors.

Example 3

Recipient Evaluation

A complete history and physical examination of the individual is performed. Estimation of pre-HSCT Lansky or Karnofsky status is obtained. The history includes: age of diagnosis, overall growth and development, frequency and number of transfusions, any aplastic crises, prior treatment (e.g., hydroxyurea), baseline HbF plus A2 levels, alloimmunization status, treatment and dates, any MRI scans, transfusion therapy, infections, aseptic necrosis, history of hepatitis, iron overload, prior liver biopsies, and pathologic findings.

The following hematological tests are performed: CBC (Hgb, Hct, MCV, MCHC, RDW, platelet, white blood cell count), differential count, reticulocyte count, ferritin, folate, quantitative Hgb electrophoresis, PT, PTT, fibrinogen, direct and indirect Coombs test. In addition, the alpha gene number is determined, the beta-globin haplotype is determined, globin chain synthetic studies are performed, and the subject is ABO Rh typed and screened.

The following chemistries are obtained: total and direct bilirubin, SGPT, SGOT, alkaline phosphatase, Protein C, IgG subclasses, albumin, Ca++/PO4++/Mg++, serum electrolytes, BUN/creatinine, urinalysis, creatinine clearance/GFR; and endocrine levels of T4, TSH, FSH, LH, and growth hormone.

The individual is HLA typed (HLA A, B, C, DQ and DR typing) based on molecular analysis.

The following diagnostic tests are performed on the individual: a CT scan (brain, sinuses, chest, abdomen, pelvis), PFTs (crying vital capacity for younger children unable to perform conventional PFT, DLCO for patients >10 years), EKG, echocardiogram or MUGA scan, liver and spleen scan, ultrasound of gall bladder, bone age, and estradiol or testosterone.

The individual is screened for the following infectious markers: CMV, IgG, PCR, HSV & VZV IgGs, HIV 1 and 2 antibody and PCR, HTLV 1 and 2 antibody, Hepatitis B surface antigen, Hepatitis B core antibody, Hepatitis C antibody and PCR, EBV IgG and IgM, *toxoplasma* IgG and IgM, West Nile Virus NAT, *Trypanosoma cruzi* (Chagas) antibody, RPR or equivalent.

Example 4

Donor Evaluation and Selection

HLA-identical donor and recipients are used, or donor and recipient mismatched pairs (e.g., up to haploidentical (parent, aunt, uncle, cousin, or sibling)) are used. Family members willing to donate bone marrow are HLA-typed. The best available match is selected. All donors participating are evaluated as per FDA regulations for donor screening prior to stem cell harvest. All evaluations are completed within 30 days of the transplant. Pediatric donors are considered for mobilization. If the donor is not a good candidate for apheresis, bone marrow is harvested from the iliac crest. If more than one related donor is available, the closer matching, younger, and/or CMV-negative donor is selected. All donors are placed on iron replacement therapy. Pheresed donors can be supplemented with Vitamin K and/or calcium.

Donors are screened as described herein and the following information is obtained. The history and physical examination of the donor is obtained including pregnancy and transfusion history. Donors are screened for CBC, differential; PT with INR, PTT and fibrinogen; ABO and Rh Type and screen, ferritin, iron and TIBC; HLA typing: HLA class I (-A, -B, -C) and class II (-DR, -DQ) typing by molecular analysis; hemoglobin electrophoresis (thalassemia trait is acceptable); SGPT or SGOT, alkaline phosphatase, and bilirubin (total and direct); serum pregnancy test; serum electrolytes, BUN, and creatinine; CMV, IgG, PCR, HSV & VZV IgG, HIV 1 and 2 antibodies and PCR, HTLV 1 and 2 antibodies, Hepatitis B surface antigen, Hepatitis B core antibody, Hepatitis C antibody and PCR, EBV IgG and IgM, *Toxoplasma* IgG and IgM, West Nile Virus NAT, *Trypanosoma cruzi* (Chagas), RPR or equivalent test; hepatitis B core antibody (if antibody-positive, perform PCR for viral DNA, accept donor if negative); hepatitis B surface antigen (reject Hepatitis B antigen positive donor); HCV antibody (positive donor is acceptable only if PCR for viral DNA is negative); Herpes Simplex Virus antibody (document status only; positive donor is not rejected); HIV I/II antibody (reject HIV I/II positive donor); HIV PCR (reject HIV PCR positive donor); HIV I/II antibody (reject HTLV I/II positive donor); CMV antibody titer (if positive and recipient is negative, consider another donor if available, otherwise CMV screening and prophylaxis is mandatory); serologic test for syphilis (if positive, perform a fluorescent treponemal antibody test; donor is accepted if fluorescent treponemal antibody is negative); chest X-ray, if the donor is greater than 21 years of age; and EKG if the donor is greater than 40 years of age.

Example 5

Pre-Transplantation Treatment of Donor

For donors, a total of 560 cc of blood will be collected for archiving of lymphocytes for immunocompetence testing. This can be obtained as a single blood donation pre-transplant (450 cc). The remaining eleven 10 cc-yellow top collection tubes are obtained eight weeks after the first donation. For pediatric bone marrow donors, no more than 3 ml/kg at any one time are drawn, and no more than 7 ml/kg over a six-week period are drawn as per the NIH guidelines for pediatric research blood draws.

Beginning day −4 (with respect to HSC+hFC infusion) and for up to +4 days, 10 ng/kg G-CSF is administered b.i.d. Collection begins on day −1. A minimum of $5 \times 10^6$ CD34/kg total is collected. A maximum of two collections are done. With each blood stem cell donation, 5-10 ml of blood is taken at the start and at the end of the procedure to measure blood cell counts including enumeration of CD 34+ cells.

At two days and one week after donation, the donor is contacted to confirm whether any adverse events have occurred. The donor also is asked to donate a blood sample (7 µl) one month after donation to ensure blood counts have recovered. The donor is treated with therapeutic iron, Vitamin K or calcium as needed. The visits for G-CSF administration, blood stem cell donations, and blood draws are summarized below in Table 4 (e.g., an X marks what will occur on each visit).

TABLE 4

| Visits | Symptom Assessment | Filgrastim/ G-CSF | Blood Stem Cell Donation | Blood Draws |
|---|---|---|---|---|
| Screening | X | | | X |
| Preparation, Day −3 | X | X | | X |
| Preparation, Day −2 | X | X | | |
| Preparation, Day −1 | X | X | | |
| Preparation, Day 0, First donation | X | X | X | X |
| Second donation* | X | | X | X |
| 2 days after donation | X | | | |
| 1 week after donation | X | | | |
| Potential blood draws to test for donor chimerism in the recipient (up to 3 years) | | | | X |

*2nd donation occurs only if sufficient cells are not obtained in the 1st collection

Example 6

Recipient Conditioning

Individuals are examined by a radiation therapist to determine dosimetry for TBI. Central venous access is established in all patients prior to initiation of conditioning. Campath-1H is administered in a first session at day −53, −52, −51, and −50 at a maximum dose of 30 mg and in a second session at a maximum dose of 20 mg administered at day −24, −23, −22, and −21. The pediatric dose of Campath is 10 mg/day on cycle one and 7 mg/day on cycle two. For smaller recipients and those less than one year of age, Campath-1H is dosed at a rounded up dose of 0.4 mg/kg for the first regimen, and at a rounded up dose of 0.3 mg/kg for the second regimen. The route of administration of the Campath, either subcutaneously or intravenously, is at the discretion of the attending physician. Start dates for Campath administration can be moved forward or backward 1-3 days to accommodate scheduling conflicts. Fludarabine is administered on day −5, −4, and −3. The individual receives TBI and begins cyclosporine immunosuppression at day −1. The second immunosuppressive medication, mycophenolate mofetil, is started the evening of HSC+hFC infusion (day 0). The conditioning regimen is shown in the following Table.

TABLE 5

Conditioning Approach

| | |
|---|---|
| Day −53 to −50 | Campath-1H is administered at 30 mg/day for adults and 10 mg/day for children over each of the four days. |
| Day −24 to −21 | Campath-1H is administered at 20 mg/day for adults and 7 mg/day for children over each of the four days. |
| Day −5 −4, −3 | Fludarabine is administered at 30 mg/m2 intravenously over a period of 30 minutes on each of these three days. |
| Day −1 | Pre-transplant conditioning 200 cGy TBI (35-40 cGy/min); Cyclosporine is administered day −1 and continued until it has been determined that the patient has engrafted, or it has been demonstrated that the patient has failed to engraft, or at the discretion of the physician. If engraftment occurs, cyclosporine is continued for at least 12 months. If there is no engraftment, cyclosporine is discontinued. Marrow is processed to retain hFC and HSC using ferromagnetic approach. |
| Day 0 | HSC + hFC is administered. MMF is started. |

The radiation is delivered at day −1. The radiation dose is 200 cGy of 6 MV accelerator X-rays, delivered in one fraction. A dose rate of 35-40 cGy/minute is used, dependent on the distance, energy, and patient dimensions. Dose variations greater than 10% are evaluated and approved on an individual basis. Infusion of the HSCs+hFCs occurs on day 0. Patients receive daily penicillin or equivalent prophylaxis for 2 years post-transplant, or longer at the discretion of the treating physician.

Example 7

HSC+hFC Cell Processing

The mobilized peripheral blood stem cells are incubated with monoclonal antibodies that are specific for alpha beta TCR T cells and B cells, then depleted by immunomagnetic separation. The composition of the infused cells is assessed by immunofluorescent staining for CD34 HSCs; CD8+/TCR−/CD56$^{dim/neg}$ hFCs; γδ T cells, and αβ-TCR+ T cells. The adequacy of cellular depletion is determined by flow cytometric analysis, and the clinician is notified of preliminary cell doses prior to infusion. The cell product also is analyzed for bacteria, fungus, and endotoxins. The HSC+hFC product is infused via a central venous line in a monitored setting per institutional guidelines.

The processed graft is administered to all subjects, and the graft is only limited based on the maximal allowable alpha beta TCR dose. However, only those subjects with a minimally acceptable graft (e.g., at least $5×10^9$ total leukocytes available from the collection to process; at least $5×10^6$ CD34/kg of recipient body weight; and a T cell depletion of less than 0.5 logs) are evaluated as described herein.

Example 8

Cell Dosing Algorithm

As many HSCs, hFCs and progenitors as possible are administered within the context of a maximal allowable T cell dose to avoid GVHD. Presently, the maximum dosing is $3.0×10^6$ to $4.2×10^6$ alpha beta T cells/kg recipient body weight (with a preferred starting point at $3.8×10^6$ alpha beta T cells/kg recipient body weight). Recipients are followed for a minimum of 28 days. If engraftment is not observed, the maximal allowable alpha beta TCR dose is increased by one unit ($4×10^5$/kg recipient body weight). The maximal allowable alpha beta TCR dose is increased until stable engraftment is achieved without significant GVHD. For HLA-matched transplants, there is no maximum T cell cap and cell dose does not increase based on the outcome of these matched transplants. For patients who are mismatched, the maximal allowable alpha beta TCR dose is determined

TABLE 6

| | |
|---|---|
| HSC, hFC, progenitors | As many as possible |
| NK cells, B cells | Record and report doses |
| γδ-TCR + T cells | Record and report doses |
| αβ-TCR + T cells | For HLA matched, there will be no cap. For HLA mismatched, the maximal allowable will be determined by the last safe dose in the kidney, heart, liver tolerance, sickle cell, and MS protocols. |

If significant (>0.5%) donor engraftment is observed in the first 28 days, the individual is followed for an additional 28 days to assess the incidence of acute GVHD.

Example 9

Additional Sickle Cell Patients Transplanted

Subject #5 was 9 years of age at the time of transplant (March 2006). He had experienced multiple pain crises, two episodes of acute chest syndrome before transplant, and had been treated with exchange transfusions for 7 years. The subject received HLA-matched trait sibling donor's iliac crest bone marrow and was conditioned with essentially the same regimen as described in Section C above. The graft contained $5.24 \times 10^6$ CD34+ cells/kg of body weight, $0.55 \times 10^6$ alpha beta-TCR$^+$ cells/kg body weight and $0.35 \times 10^6$ FC cells/kg body weight. The subject has been transfusion-independent post-stem cell transplant with 100% donor RBC production and chimerism levels at 20-30% donor by FISH for greater than 1525 days post-transplant. Immunosuppression was discontinued at 23 months post-transplant. Subject has not exhibited graft-versus-host disease (GVHD), transplant-related toxicity, or sickle cell complications since transplant.

Subject #7 was a 16-year-old male who experienced repeated acute chest syndrome episodes that required red blood cell transfusion therapy. Prior to undergoing the transplant in September 2009, he was hospitalized for osteomyelitis of the right knee and multiple vaso-occlusive painful events. The subject received a haploidentical transplant from his parent. The subject was conditioned essentially as described above in Section C. The subject tolerated the conditioning well and the transplant was uneventful. He received $3.26 \times 10^6$ CD34+ cells/kg body weight, $3.8 \times 10^6$ alpha beta TCR+ cells/kg body weight, and $0.5 \times 10^6$ FC cells/kg body weight, and he was managed as an outpatient. Unfortunately, this subject was not compliant in the immediate post-transplant period and did not regularly take cyclosporine and MMF as required. Chimerism was not present at post-transplant months 1 and 2. Post-transplant, he experienced a recurrent pain crisis that subsequently resolved. The subject remains on the study to monitor for adverse events, but chimerism testing was discontinued after post-transplant month two.

Subject #8 was a 12-year-old female who experienced numerous hospitalizations for pain crises. She also had undergone a splenectomy following sequestration and cholcystectomy. She underwent conditioning essentially as described above in Section C, and she received a haploidentical transplant from her parent, who had the SCD trait. She received $19.1 \times 10^6$ CD34+ cells/kg body weight, $3.8 \times 10^6$ alpha beta TCR+ cells/kg body weight, and $0.79 \times 10^6$ FCs/kg body weight, and, following transplantation, she was managed as an outpatient. She tolerated the conditioning very well and demonstrated robust donor engraftment of 71% at one month post-transplant. Her whole blood chimerism remained durable at 84%, with lymphoid chimerism at 58% and myeloid chimerism at 95% at month nine. She was producing 100% donor RBC as reflected by hemoglobin A at 57%, hemoglobin S at 41%, and hemoglobin A2 at 2% as demonstrated by hemoglobin electrophoresis. The subject has not required transfusion therapy since transplant and is asymptomatic. She has had no evidence for GVHD.

Subject #9 was a 25-year-old male who experienced repeated PRBC transfusions, cholecystectomy with sickle cell disease, hypertension and renal vascular disease prior to transplant. The subject was conditioned essentially as described above in Section C, and he tolerated the conditioning well. The alpha beta TCR+ cells for this subject was increased to $4.2 \times 10^6$ cells/kg body weight, and the subject also received $1.46 \times 10^6$ CD34+ cells/kg body weight and $0.72 \times 10^6$ FCs/kg body weight. He demonstrated 10% donor chimerism at post-transplant month one. His chimerism decreased to 4% at month two and to less than 2% at day 100. The subject was admitted for elevated creatinine due to calcineurin inhibitor (CNI) sensitivity in the second post-transplant month. The dose was adjusted and the SAE resolved. About one month later, he was admitted for fever, gram positive cocci, and CMV infection. He went off study to participate in an investigational drug for CMV treatment.

Section E—Prevention of Graft vs. Host Disease (GVHD) Following Solid Organ Transplant Example 1

Patient Recruitment

Candidates for the protocol were selected from the list of patients awaiting renal transplantation or who were being evaluated for transplantation. This selection process was carried out by the transplant surgeons and the transplant nurse coordinators of the Institute of Cellular Therapeutics at the University of Louisville ("the Institute").

Example 2

Inclusion Criteria

A candidate patient must be between the ages of 18 and 65 years and meet the Institution's criteria for renal transplantation for end-organ failure. A candidate patient must be receiving his or her first renal transplant. A candidate patient must be receiving a renal transplant only. The crossmatch must be negative between the donor and the recipient. Women who are of child bearing potential must have a negative pregnancy test (urine test is acceptable) within 48 hours prior to initiating TBI and must agree to use reliable contraception for 1 year following transplant. Candidate patients must exhibit no evidence of donor-specific antibody, presently or historically.

Example 3

Exclusion Criteria

Patients are not candidates if they have a clinically active bacterial, fungal, viral or parasitic infection, or if they are pregnant. Patients are not eligible if they exhibit clinical or serologic evidence of viral infection that would preclude the recipient from receiving a kidney transplant. A patient is not a candidate if they have received previous radiation therapy at a dose which would preclude TBI, if there is a positive crossmatch between the donor and the recipient, or if there is evidence for immunologic memory against the donor. Patients also are excluded if their body mass index (BMI) is less than 18 or greater than 35.

Example 4

Donor Selection Criteria

Donors for this protocol must meet all of the Institute's criteria for renal and stem cell transplant.

Example 5

Protocol

The timing for all manipulations is relative to the TBI conditioning of the recipient on day 0. Beginning day −3 and for up to four days, 10 ng/kg G-CSF was administered b.i.d. Collection began on day 0. On day 0, a CD34 count was performed prior to giving the final dose of G-CSF. HSC+hFC transplantation was scheduled 4 to 6 weeks prior to the desired date of kidney harvest. The donation and transplant of the kidney is not schedules until the donor's platelet counts have returned to baseline and safe levels for kidney donation (e.g., greater than 100,000/μl of whole blood).

The visits for G-CSF administration, blood stem cell donations, and blood draws are summarized in Table 7 The 'X' marks what will occur on each visit.

TABLE 7

Donor Mobilization

| Visits | Symptom Assessment | Filgrastim/ G-CSF | Blood Stem Cell Donation | Blood Draws |
|---|---|---|---|---|
| Screening | X | | | X |
| Preparation, Day −3 | X | X | | X |
| Preparation, Day −2 | X | X | | |
| Preparation, Day −1 | X | X | | |
| Preparation, Day 0, First donation | X | X | X | X |
| 2 Days after donation | X | | | |
| 1 Week after donation | X | | | |
| Potential blood draws to test for donor chimerism in the recipient (up to three years) | | | | X |

Example 6

Pre-Transplant Conditioning

Cell dose (HSC+hFC) as well as degree and type of conditioning of the recipient were independent variables that influence engraftment. In the current protocol, cell dose and conditioning were optimized until >1% donor chimerism was established. The initial target cell dose for HSC+hFC was >1×10$^8$ CD34+/kg. The first patients received 200 cGy TBI, fludarabine (30 mg/m$^2$ day −3 to −1), and post-transplant immunosuppression with MMF (15 mg/kg q 12 h beginning day 0), and FK506 (0.02 mg/kg q 12 h beginning day −1) for six months, or as clinical need required. The decision to use either FK506 (tacrolimus) or cyclosporine was left to the physician because patients differ in their ability to tolerate either drug. The marrow was infused on day +1. The schedule is shown in Table 8.

TABLE 8

| Day | Treatment | Dose |
|---|---|---|
| −3 | Fludarabine after dialysis (if required) | 30 mg/m2 |
| −2 | Fludarabine after dialysis (if required) | 30 mg/m2 |
| −1 | Fludarabine | 30 mg/m2 |
| 0 | Start MMF and FK506 or cyclosporine | |
| 0 | TBI (200 cGy) | 35-40 cGy/min |
| | Harvest donor marrow and process to obtain HSC + hFC | |
| +1 | Infuse HSC + hFC after dialysis (if required) | |
| +28-60 | Renal transplantation; continue MMF and calcineurin inhibitors | |

If the recipient required dialysis, the dosing of fludarabine and the HSC+hFC infusion occurred after dialysis on the specified days. On the morning of HSC+hFC infusion, an extra liter of volume was removed from dialysis to account for the volume of HSC+hFC. Dialysis then was scheduled for 48 hrs or later following HSC+hFC infusion to give the cells an optimum opportunity to home to the marrow compartment.

Example 7

Outcomes

A minimum of about 2 weeks post-HSC+hFC infusion or as long as the recipient needs to fully recover from the stem cell transplant procedure passed before the renal transplant was performed from the same donor. The following algorithm was used based on the outcome of the HSC+hFC transplant.

1) if the recipient exhibited chimerism of ≥1% and was determined to be tolerant to the donor, at least six months of Prograf and MMF was administered while donor:host tolerance to the kidney is established. The recipient did not receive Campath-1H or any additional immunosuppression at the time of transplant.

2) if the recipient did not engraft, the patient as tested by flow crossmatch prior to transplant to ensure no donor-specific antibodies developed. If no donor-specific antibody was present, the patient underwent living donor kidney transplant using conventional lymphodepletion induction with Campath-1H followed by maintenance immunosuppression with FK506 and MMF. Other lymphodepletion approaches for induction therapy such as ALG can be used in place of Campath per standard of care.

3) if donor-specific antibody developed, the patient was assessed and a clinically appropriate antibody reduction protocol implemented prior to transplantation. Patient sensitization was not expected.

Example 8

Cell Dosing Algorithm

The goal of the study was to engineer a graft with adequate HSCs, hFCs and progenitors for allogeneic engraftment while avoiding GVHD. A cell dosing algorithm was established that is tied to the maximum allowable alpha beta T cell dose. For example, if toxicity (GVHD) did not occur but engraftment was not durable, the maximum allowable T cell dose was increased by 1 unit (see below). The maximal allowable T cell dose containing as many HSCs, hFCs, and progenitors was administered. The algorithm that was used is shown in Table 9.

TABLE 9

| HSC, hFC, progenitors | As many as possible |
|---|---|
| alpha beta TCR + T cells | For HLA matched, there is no cap. For HLA mismatched, the maximal allowable is determined by the last safe dose in the kidney, heart, liver tolerance, sickle cell, and MS protocol |
| NK cells, B cells | Record and report doses |
| gamma delta TCR + T cells | Record and report doses |

The present cell dosing currently allows a maximum of 3.0×10$^6$ to 4.2×10$^6$ alpha beta T cells/kg recipient body weight; 3.8×10$^6$ alpha beta T cells/kg recipient body weight was the starting dose. Each patient was followed for at least 28 days. If no evidence of engraftment was observed, the maximal allowable alpha beta-TCR dose was increased by one unit (4×10$^5$/kg recipient body weight). The maximal allowable alpha beta-TCR dose was increased in subjects until stable engraftment was achieved without significant GVHD. For HLA-matched transplants, there was no maximum T cell cap and cell dose was not increased based on the outcome of the matched transplants. For patients who are mismatched, the maximal allowable alpha beta-TCR dose was determined If significant (>0.5%) donor engraftment was observed in the first 28 days, the subject was followed for an additional 28 days to assess the incidence of acute GVHD before the cell dose was increased. It was expected that the majority of cases of acute GVHD would be apparent by 8 weeks post-transplant. If evidence of severe GVHD was seen, the maximal allowable T cell dose was reduced to a level proven safe. To date, GVHD has not been observed.

Example 9

HSCs+hFCs

Donor PBMC was processed to enrich for hFCs and HSC. Approximately 85% of total bone marrow composition was removed, including GVHD-producing T-cells and B-cells, using a ferromagnetic approach. The resultant product was enriched for hFCs, HSCs and progenitors. After the adequacy of the processing was confirmed by flow cytometry, the HSC+hFC graft was approved for infusion. A delay in the bone marrow transplantation of up to 72 hours following donor cell harvest was accepted to allow for bone marrow processing and transplantation. Dose-adjusted Bactrim and Valcyte (if CMV+) or Valtrex (if CMV-) prophylaxis was started. The patient was carefully monitored during and after infusion of marrow to detect any changes in, for example, respiration, blood pressure, or angioedema, which may be an indication of hypersensitivity.

Example 10

Post-Transplant Immunosuppression

Subjects enrolled in this protocol received standard immunosuppression at the discretion of the attending physician and according to institutional protocol. For deceased donor kidney/HSC+hFC recipients and living donor HSC+hFC recipients without demonstrable donor chimerism at 1 month, this generally included Prograf plus MMF after lymphodepletion induction therapy with ALG or Campath. Prograf levels were maintained between 8-12 ng/ml. Starting on day 0, MMF was generally dosed at 1-1.5 gms b.i.d. A one time dose of Campath, 30 mg IV, was optionally given in the operating room. SoluMedrol was given at a dose of 500 mg IV in the operating room one hour prior to the Campath dose, then post-operatively on day 1 at a dose of 250 mg IV and on post op day 2 at a dose of 125 mg. FK506 and MMF were continued for at least 6 months in patients who were chimeric to promote engraftment and tolerance induction.

Example 11

Preliminary Solid Organ Transplant Protocol

Preliminary experiments demonstrated the success and safety of HSCs+hFCs and immune-based nonmyeloablative conditioning in renal transplant recipients. Dosing of the HSCs+hFCs was performed to maximize safety and optimize HSC and hFC content. The overall goal was to completely avoid GVHD. Solid organ tolerance protocols were begun with a maximum of $0.2 \times 10^6$ T cells/kg recipient body weight to perform a dose-escalation. Total alpha beta T cells were used in the dose-escalation experiments since the other effector cells for GVHD (NK, B-cells, and APC) are all present in amounts proportional to total alpha beta T cells. CD34 and hFC dose were optimized within the maximum allowable T cell dose. No significant immunologic events (i.e., rejection episodes or antibody production) were observed in any of the patients. None of the patients developed GVHD, but only transient chimerism was observed.

Since September 2004, nine heart and eleven kidney patients have been transplanted using the dose-escalation strategy set forth in Table 10. Patients 5, 6, 12, and 13, which are highlighted in Table 10, are described in more detail; three patients underwent simultaneous kidney/HSC+hFC transplantation from living donors and the remaining patient received his kidney from a deceased donor. All four patients were conditioned with 200 cGy TBI and underwent lymphodepletion induction therapy with Campath followed by maintenance immunosuppression with MMF and a calcineurin inhibitor. They did not receive fludarabine. The 4 patients are briefly described below.

Patient #5 is a 55-year-old male who underwent a deceased donor renal allograft/HSC+hFC transplant in September 2005. The patient received $3.7 \times 10^6$ CD34 and $0.8 \times 10^6$ hFC per kg recipient body weight. The conditioning was well tolerated and no adverse events related to the approach occurred. The donor and recipient shared a 1/6 HLA-antigen match. The patient experienced the anticipated nadir, and then recovered immune function and endogenous hematopoiesis. He is doing well with a recent serum creatinine of 2.1.

Patient #6 is a 58-year-old male who underwent a living donor kidney/HSC+hFC transplant from an unrelated friend in November 2005. The patient received $1.33 \times 10^6$ CD34 and $0.18 \times 10^6$ hFC per kg recipient body weight. The conditioning was well tolerated and no adverse events related to the approach occurred. The donor and recipient shared a 1/6 HLA-antigen match. The patient experienced the anticipated nadir, and then recovered immune function and endogenous hematopoiesis. He is doing well, with a recent serum creatinine of 2.0.

Patient #12 is a 37-year-old female who underwent a living donor kidney/HSC+hFC transplant from her cousin in October 2007. She received $2.24 \times 10^6$ CD34 and $0.41 \times 10^6$ hFC per kg recipient body weight. The conditioning was well tolerated and no adverse events related to the approach occurred. The donor and recipient shared a 2/6 HLA-antigen match. The patient experienced the anticipated nadir, and then recovered immune function and endogenous hematopoiesis. She is doing well with a recent creatinine of 1.2.

Patient #13 is a 49-year-old female who underwent a kidney/HSC+hFC transplant from her brother in November 2007. The patient received $3.85 \times 10^6$ CD34 and $0.78 \; 10^6$ hFC per kg recipient body weight. The conditioning was well tolerated and no adverse events related to the approach occurred. The donor and recipient shared a 4/6 HLA-antigen match. The patient experienced the anticipated nadir, and then recovered immune function and endogenous hematopoiesis. She is doing well with a recent creatinine of 1.2.

TABLE 10

Cell dosing for patients (per kg recipient weight)

| # | Transplant | Date of Transplant | Source | TBI (cGy) | T cells* | CD34* | hFC* |
|---|---|---|---|---|---|---|---|
| 1 | Heart | September 2004 | VB | 200 | 0.2 | 1.99 | 0.23 |
| 2 | Kidney | October 2004 | MPB | 200 | 0.2 | 0.78 | 0.02 |
| 3 | Heart | December 2004 | VB | 200 | 0.4 | 5.70 | 1.07 |
| 4 | Kidney | February 2005 | VB | 200 | 0.6 | 3.80 | 0.14 |

TABLE 10-continued

Cell dosing for patients (per kg recipient weight)

| # | Trans-plant | Date of Transplant | Source | TBI (cGy) | T cells* | CD34* | hFC* |
|---|---|---|---|---|---|---|---|
| 5 | Kidney | September 2005 | VB | 200 | 0.8 | 3.70 | 0.80 |
| 6 | Kidney | November 2005 | MPB | 200 | 1.0 | 1.33 | 0.18 |
| 7 | Heart | March 2006 | VB | 200 | 1.2 | 0.71 | 0.08 |
| 8 | Heart | March 2006 | VB | 200 | 1.2 | 5.60 | 0.74 |
| 9 | Heart | May 2006 | VB | 200 | 1.4 | 4.69 | 0.55 |
| 10 | Heart | February 2007 | VB | 200 | 1.8 | 3.81 | 0.72 |
| 11 | Heart | August 2007 | VB | 200 | 1.8 | 2.08 | 0.75 |
| 12 | Kidney | October 2007 | MPB | 200 | 2.2 | 2.24 | 0.41 |
| 13 | Kidney | November 2007 | MPB | 200 | 2.2 | 3.85 | 0.78 |
| 14 | Heart | January 2008 | VB | 200 | 2.6 | 2.67 | 1.61 |
| 15 | Kidney | March 2008 | MPB | 200 | 3.0 | 9.26 | 9.34 |
| 16 | Kidney | April 2008 | MPB | 200 | 3.0 | 1.45 | 5.81 |
| 17 | Heart | April 2008 | VB | 200 | 3.4 | 4.86 | 1.87 |
| 18 | Kidney | February 2009 | IC | 200 | 0.96 | 0.90 | 0.16 |
| 19 | Kidney | April 2009 | MPB | 200 | 3.8 | 2.53 | 4.48 |
| 20 | Kidney | May 2009 | MPB | 200 | 3.8 | 3.60 | 0.90 |

*$\times 10^6$ cells; VB = vertebral body; MPB = mobilized peripheral blood; IC = iliac crest Example 12

Results of Preliminary Protocol

Initially, the chimerism observed was low (<0.2%) and only transient. However, as the total cell dose was increased, durable mixed chimerism was achieved. The immune response to the graft was modulated by the marrow infusion as evidenced by transient donor-specific tolerance in mixed lymphocyte reaction (MLR) assays observed in the more recently transplanted patients and the absence of any clinical or histologic rejection episodes.

Figure 9A:
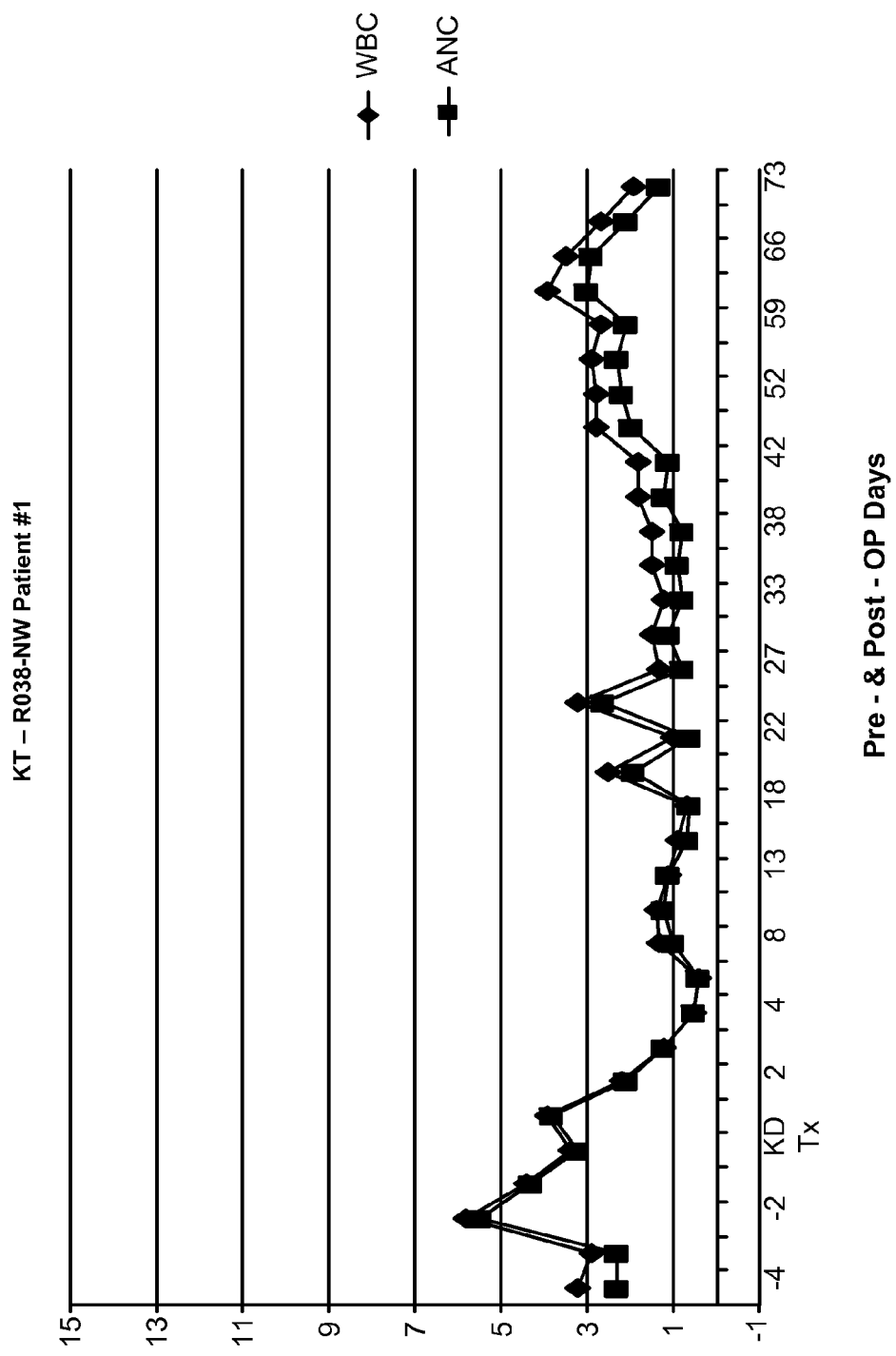
FIG. 9 are graphs showing the amount of the ANC and white blood cells (WBCs) (Panel A), the platelet count (Panel B), and the percent chimerism (Panel C) in a patient following solid organ transplant.
Figure 9B:
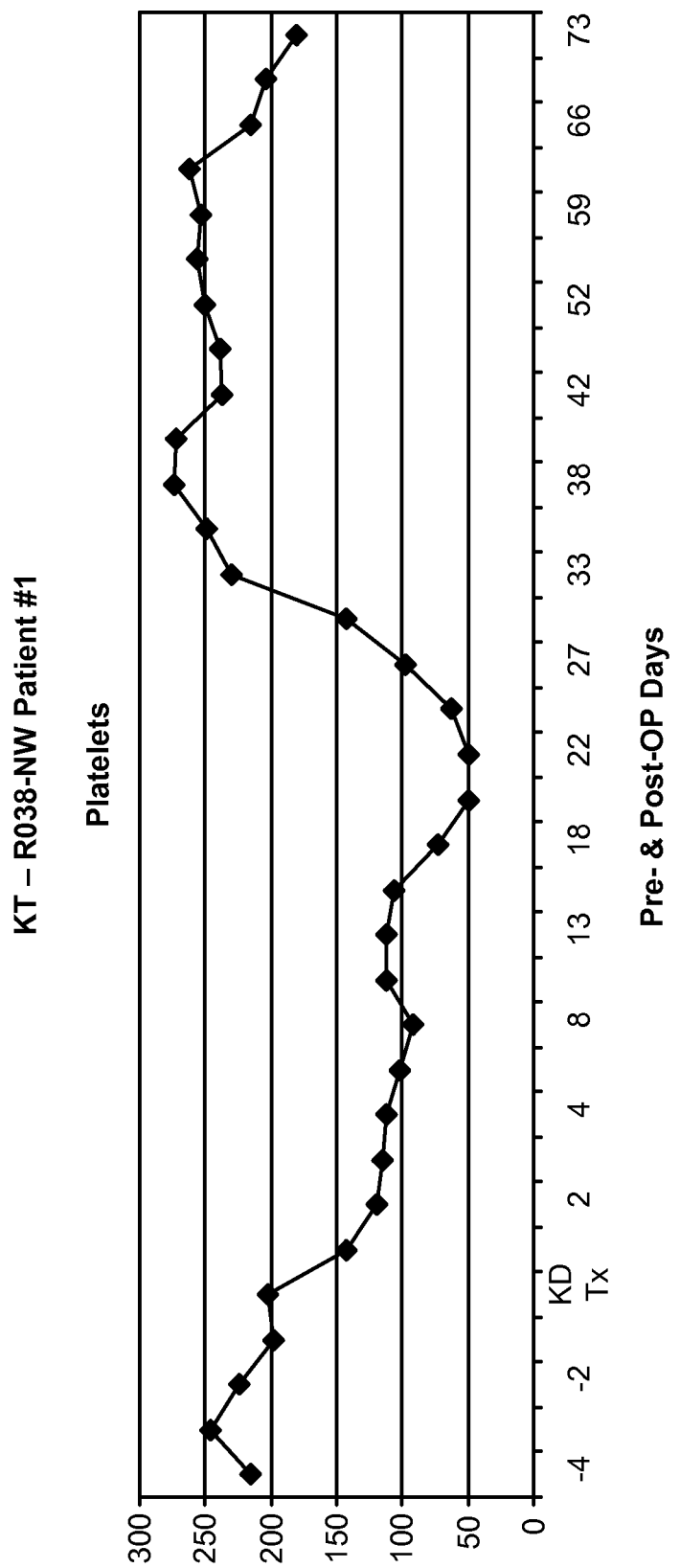
Figure 9C:
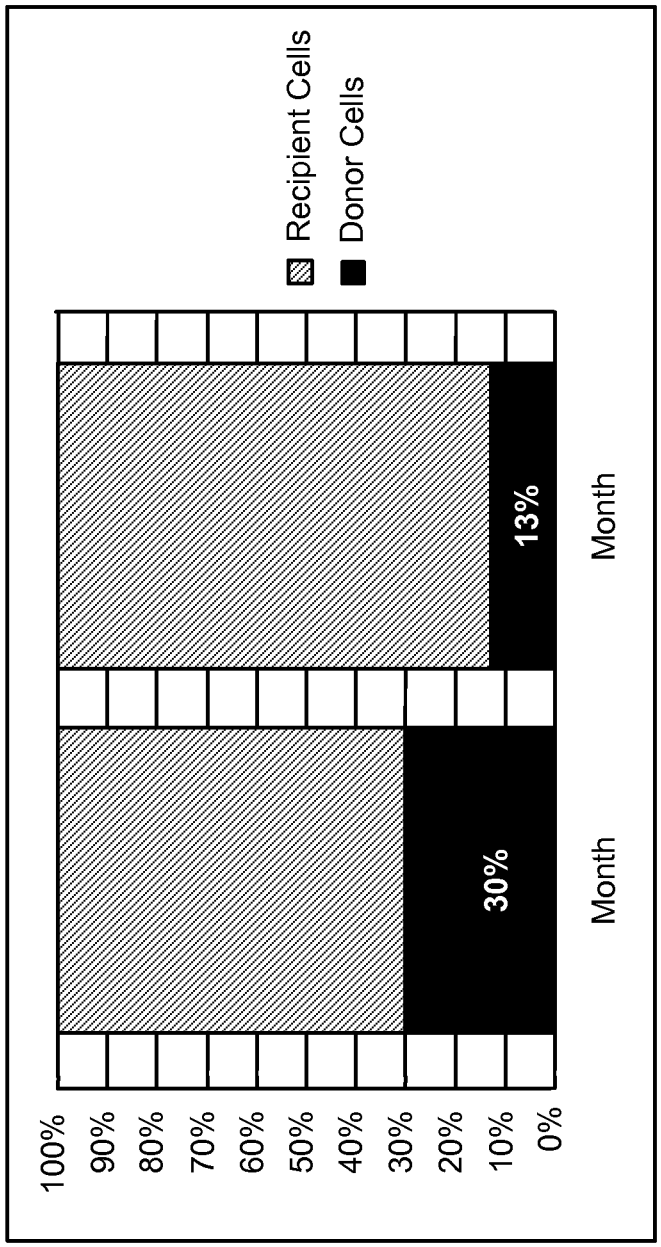
Figure 10A:
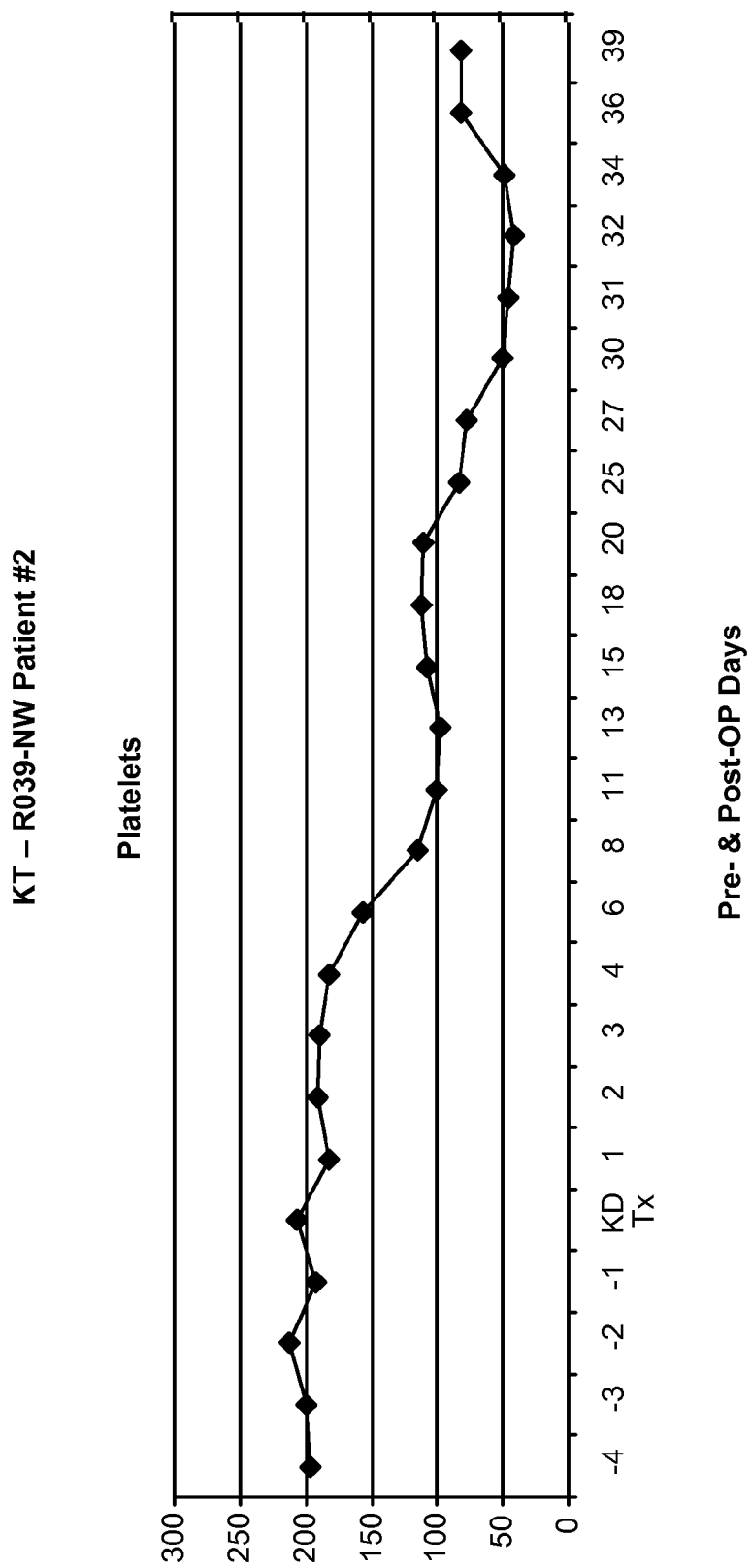
FIG. 10A is a graph showing the platelet count and FIG. 10B is a graph showing the percent chimerism in patient #2 following solid organ transplant.
Figure 10B:
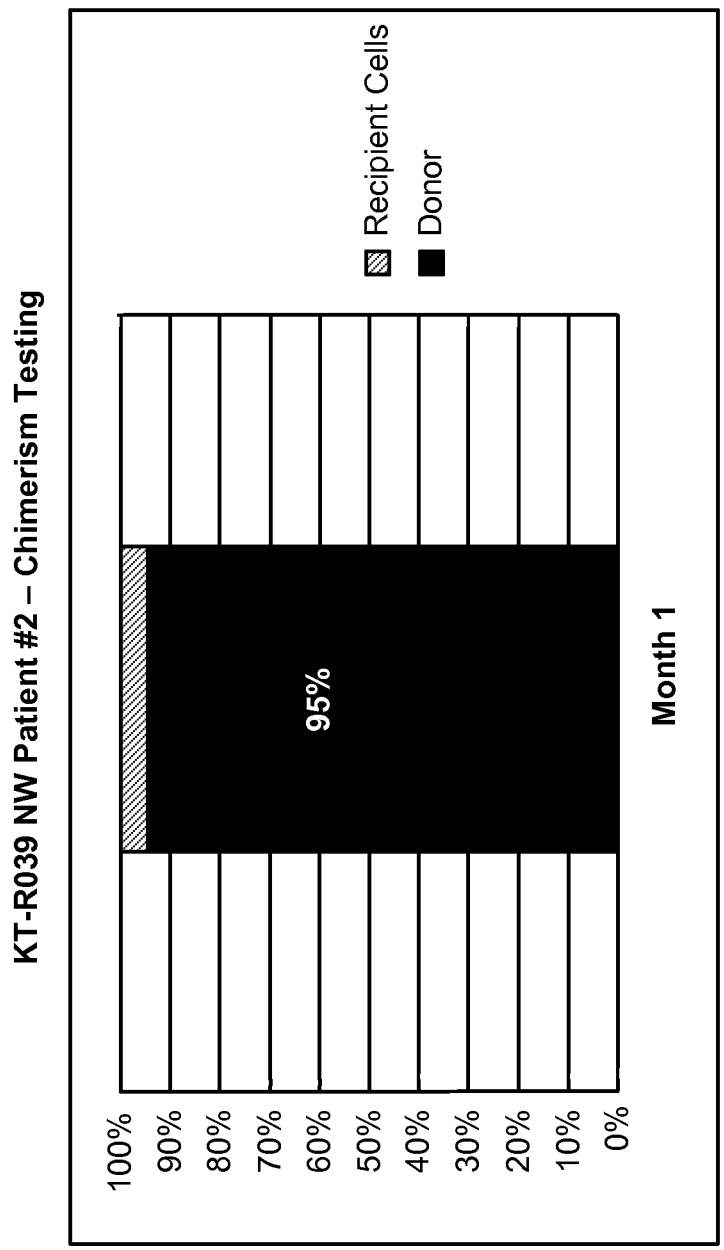
Figure 11A:
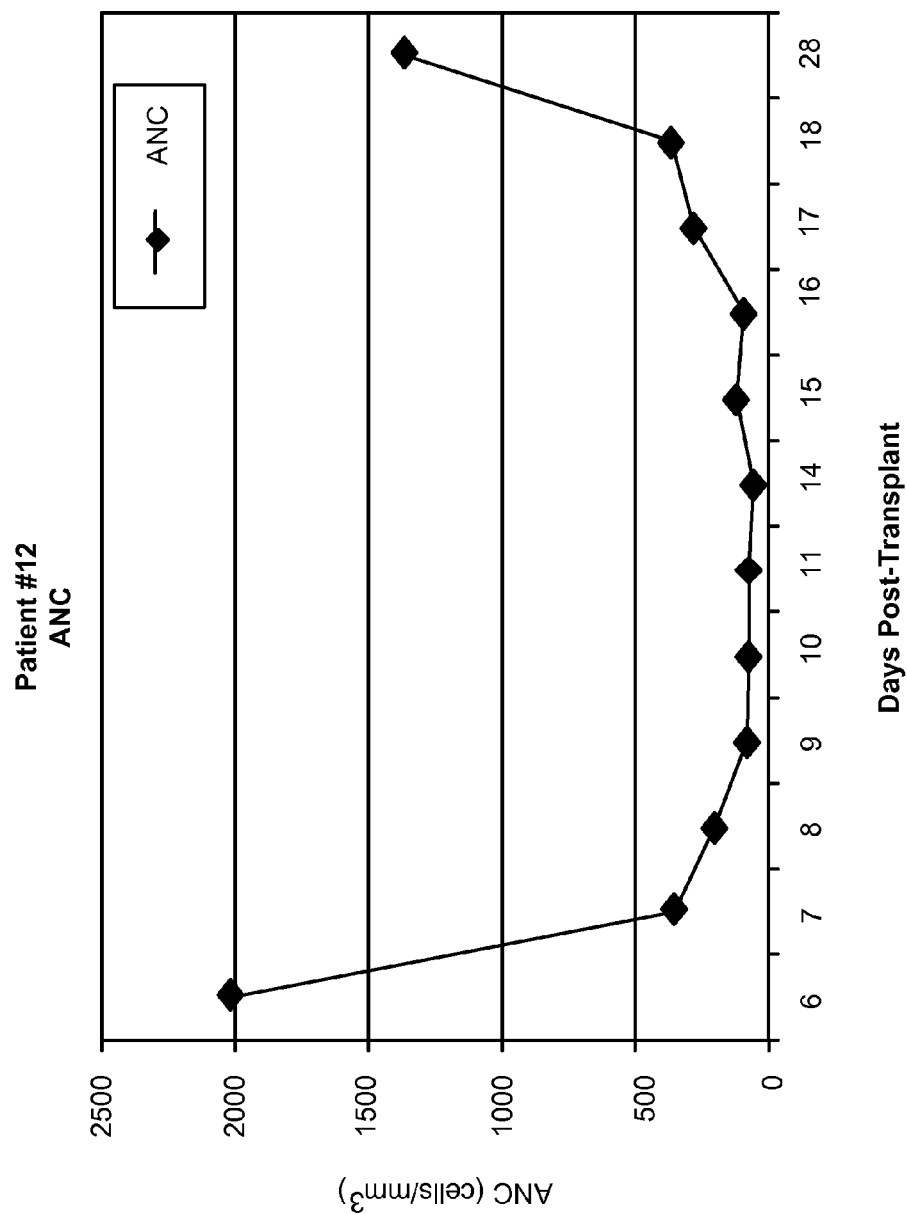
FIG. 11 are graphs showing the ANC (Panel A), the recovery of B cells, CD4+ cells, and CD8+ cells (Panel B), and the platelet count (Panel C) following solid organ transplant in patient #12.
Figure 11B:
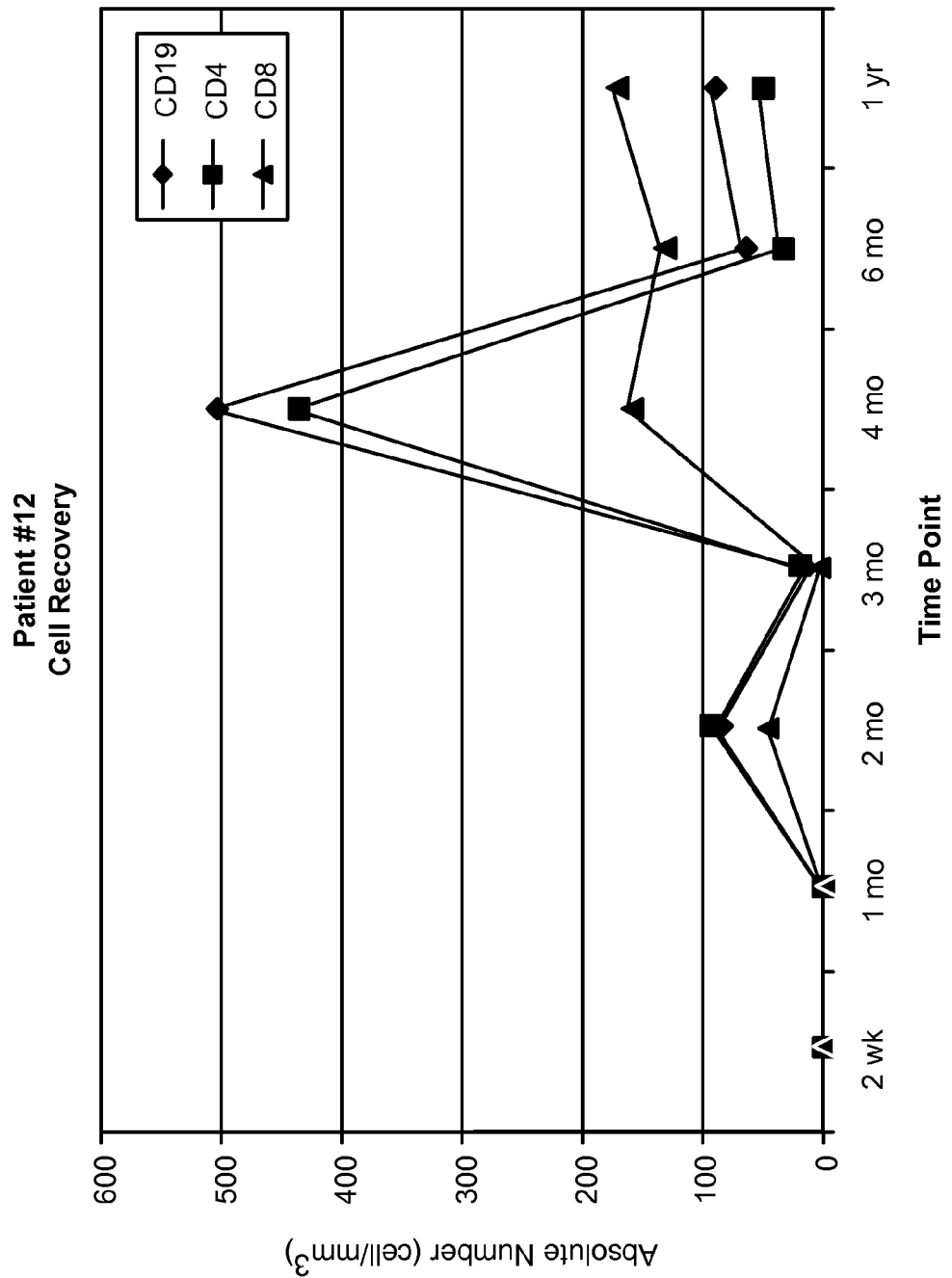
Figure 11C:
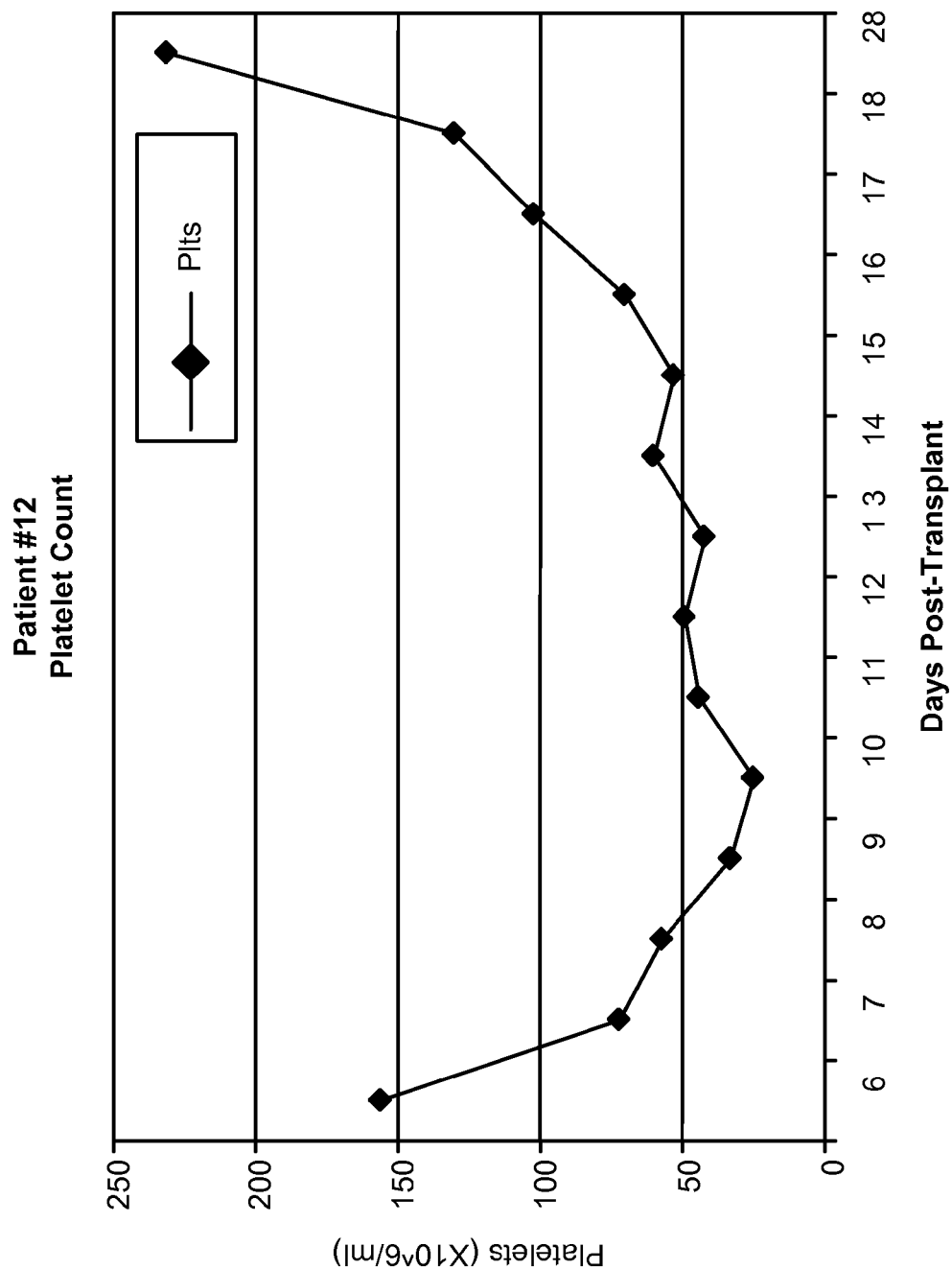

The fact that endogenous hematopoiesis resumed in those patients who did not engraft confirmed the non-myeloablative nature of the conditioning. There was an expected nadir of absolute neutrophil count (ANC) of less than 1,000 that occurred in the recipients between 7 and 18 days (FIGS. 9A and 11A), which was managed as an outpatient in Patient #12. It was found that administration of G-CSF did not accelerate recovery. The MMF and FK506 was continued through the nadir to promote engraftment. Recovery of B cells (CD19), CD4+ cells, and CD8+ cells occurred by 3 months in the Campath-lymphodepleted recipient #12 (FIG. 11B). Platelet counts were determined following solid organ transplant (FIGS. 9B, 10A, and 11C). The platelet nadir, if present, typically was brief and usually did not require transfusion therapy. The chimerism that was established in solid transplant patients is shown in FIGS. 9C and 10B.

Example 13

Modified Protocol for Solid Organ Transplant

The kidney/HSC+hFC transplant protocol was modified to add fludarabine conditioning and to perform the living donor transplants sequentially, with HSC+hFC administered one month prior to the kidney graft placement.

The first transplant (stage 1 FCRx) was performed in March 2008 (Patient #15 in Table 10). She is a 31-year-old female whose husband was her donor. The patient is currently in her nadir period and is doing well as an outpatient. A flow crossmatch performed on day 14 was negative (Table 11). In this assay, the binding of antibodies to donor T and B cells was measured by flow cytometric analysis in MCDF units.

TABLE 11

Flow Crossmatch

| | T cell | | | B cell | | |
|---|---|---|---|---|---|---|
| | % T cells | MCDF | Positive/Negative | % B cells | MCDF | Positive/Negative |
| Negative control | 57 | 250 | − | 5 | 301 | − |
| Positive control | 52 | 495 | + | 5 | 534 | + |
| Patient #15 | 54 | 245 | − | 5 | 246 | − |
| Patient #15 | 52 | 252 | − | 5 | 266 | − |

These results demonstrated the safety of the non-myeloablative conditioning and the feasibility of the HSC+hFC process and product in solid organ transplant. It is noted that none of the recipients became sensitized to the donor.

Section F—Kidney Transplant

Example 1

Donor and Recipient Eligibility

All protocols were approved by the Northwestern Institutional Review Board, the FDA IND 13881, and informed consent was obtained for all donors and recipients. Donors and recipients had to meet Institutional criteria as suitable living transplant donors and recipients; participants had to complete all phases of the pre-transplant donor and recipient evaluation to be considered for study participation. Inclusion criteria for transplant recipients included age between 18 and 65 years, absence of any donor-specific antibodies as assessed by flow PRA analysis, and receiving only a living donor kidney transplant. Women of childbearing age had to have a negative pregnancy test (urine testing acceptable) within 48 hours of receiving TBI and agree to use reliable contraception for a year after the transplantation. Exclusion criteria included clinically active bacterial, fungal, viral or parasitic infection, pregnancy, previous radiation therapy at a dose which would preclude TBI, a positive flow cytometry crossmatch between donor and recipient, presence of donor-specific antibodies, body mass index (BMI)>35 or <18, and positive serologies for HBV, HCV, and HIV.

Example 2

Conditioning and Donor Product Preparation

Figure 12:
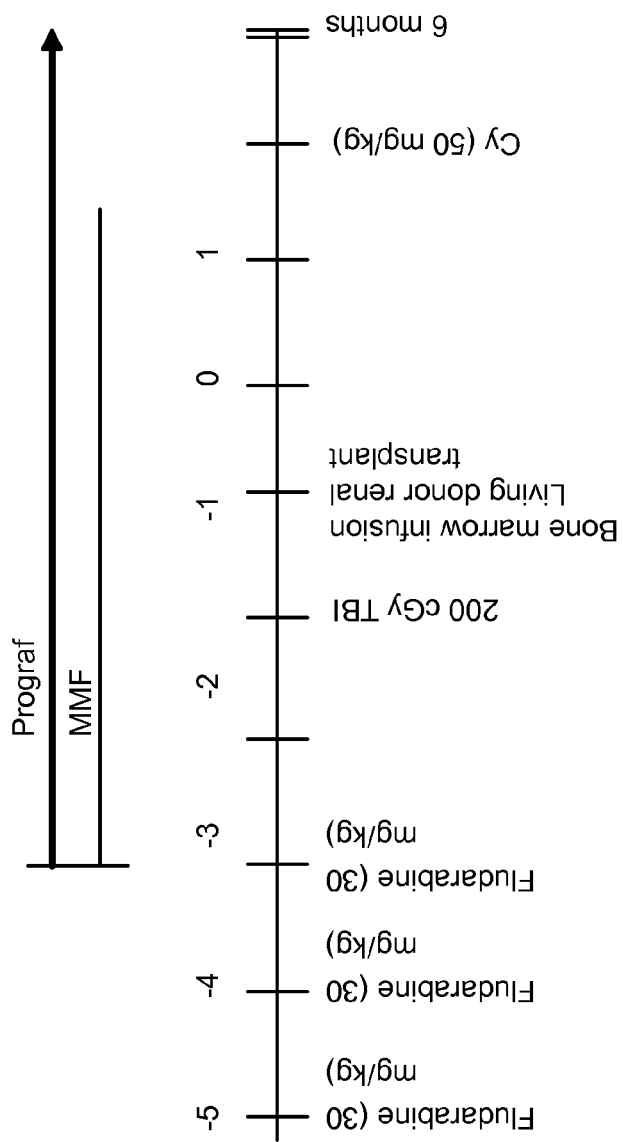
FIG. 12 is a schematic showing a general nonmyeloablative conditioning and post-transplant immunosuppression regimen as exemplified herein.

Conditioning consisted of three doses of fludarabine (30/mg/kg/dose) at days −4, −3, −2; two doses of cyclophosphamide (Cytoxan; 50 mg/kg/dose) at days −3 and +3; and 200 cGy TBI at day −1 relative to the renal transplant as depicted in FIG. 12. Hemodialysis was performed 6-8 h after the administration of fludarabine and Cytoxan. Tacrolimus (target trough concentrations 8-12 ng/ml) and mycophenolate mofetil (MMF) (Cellcept; 1 gm orally twice daily if recipient weighs <80 kg, 1.25 gm twice daily if recipient weighs >80 kg) were started at day −3 and continued throughout. HSCs+hFCs can be administered to the recipient at day 0 (i.e., the same day as the transplant) or at day +1.

Example 3

Hematopoietic Stem Cell Collection

At least two weeks prior to the renal transplant, donors were mobilized with granulocyte colony stimulating factor (G-CSF) at 10 mcg/kg b.i.d. and apheresis was performed on day +4. The product was transported by courier to the Institute for Cellular Therapeutics (ICT) and processed to remove mature graft-versus-host disease (GVHD)-producing cells while retaining hematopoietic stem cells (HSC), facilitating cells (FCs), and progenitor cells. The product was then shipped back to Northwestern University for infusion, either as a fresh product or cryopreserved.

Example 4

Immunologic Monitoring

The recipient response to PHA, Candida, tetanus toxoid, donor and third-party alloantigens was tested monthly (see, for example, Patel et al., 2008, *J. Allergy Clin. Immunol.*, 122:1185-93). Flow crossmatch assay to detect donor antibodies were performed at 1 and 6 months. Chimerism testing was performed by molecular assay using short tandem repeats (Akpinar et al., 2005, *Transplant.*, 79:236-9). Surveillance biopsies were performed at 1 year. At selected time points, immunophenotypic analysis of peripheral blood was performed for T cell, B cell, NK cell, monocytes, $CD4^+/CD25^+$ Fox $P3^+$ regulatory T cell ($T_{reg}$), and T effector cell ($T_{eff}$) recovery.

Example 5

Chimerism Testing

Chimerism was determined by genotyping of simple sequence-length polymorphisms encoding short tandem repeats (STR). For lineage chimerism testing, $CD19^+$ (B cells), $CD3^+$ (T cells), and $CD66B^+$ myeloid cells were sorted from whole blood then analyzed by molecular STR typing.

Example 6

Weaning of Immunosuppression

Prograf and MMF were continued per standard of care until 6 months post-transplant. At that point, if chimerism or donor-specific tolerance were present, the MMF was first discontinued, then the Prograf was tapered off over to subtherapeutic amounts the next few months (e.g., <3.0 ng/ml by 9 months). Prograf was discontinued at 12 months if evidence of chimerism and/or in vitro donor specific hyporesponsiveness is present.

Example 7

Results

A summary of Subject #1-Subject #9 is shown below in Table 12, and Table 13 shows the cell dosing regimens. A few of the subjects are discussed in more detail as follows.

Figure 13A:
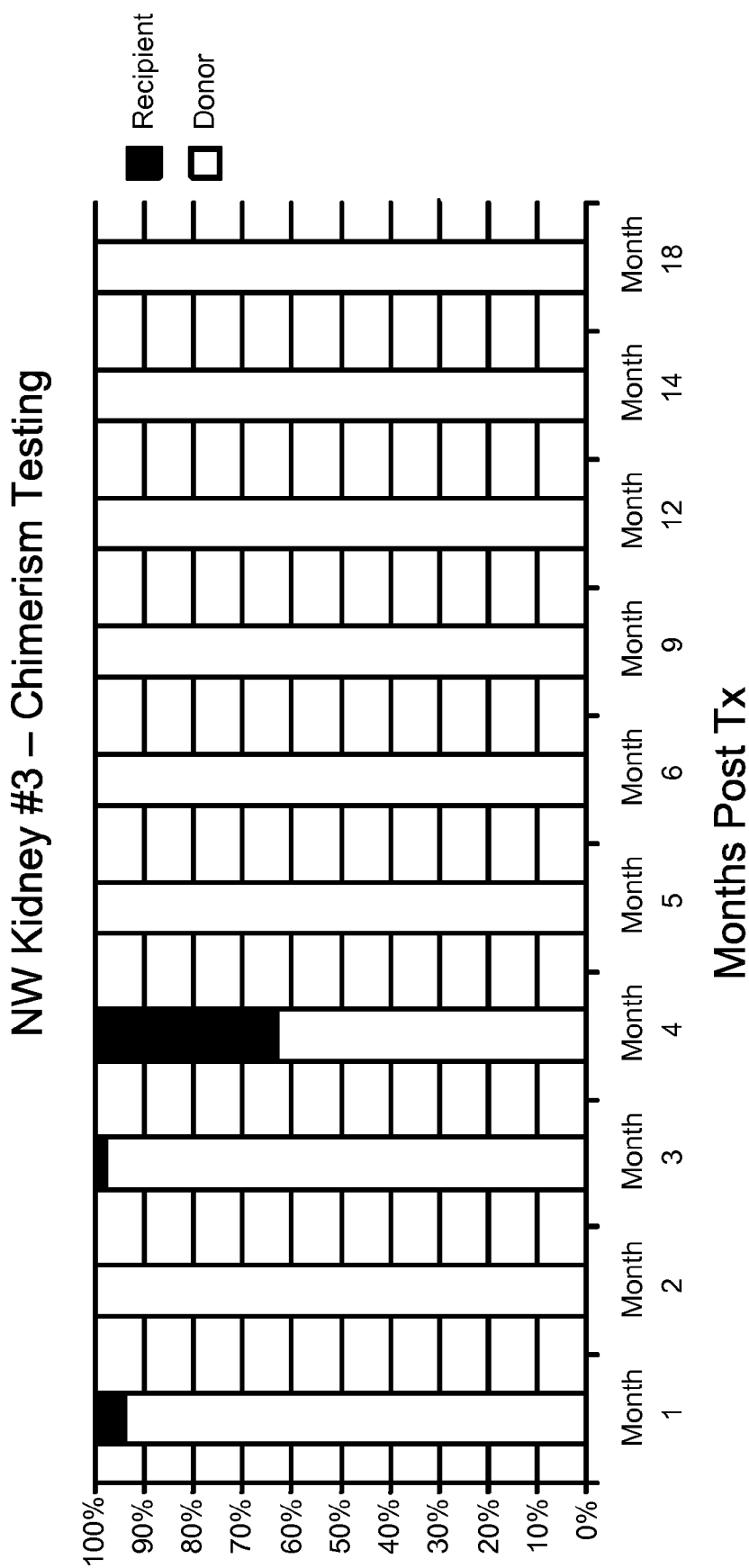
FIG. 13 are graphs showing the chimerism (Panel A), multilineage chimerism (Panel B), response to a number of stimulators (Panel C), creatinine levels (Panel D), platelet count (Panel E), and white blood count and ANC (Panel F) in living donor kidney transplant Subject #3.
Figure 13B:
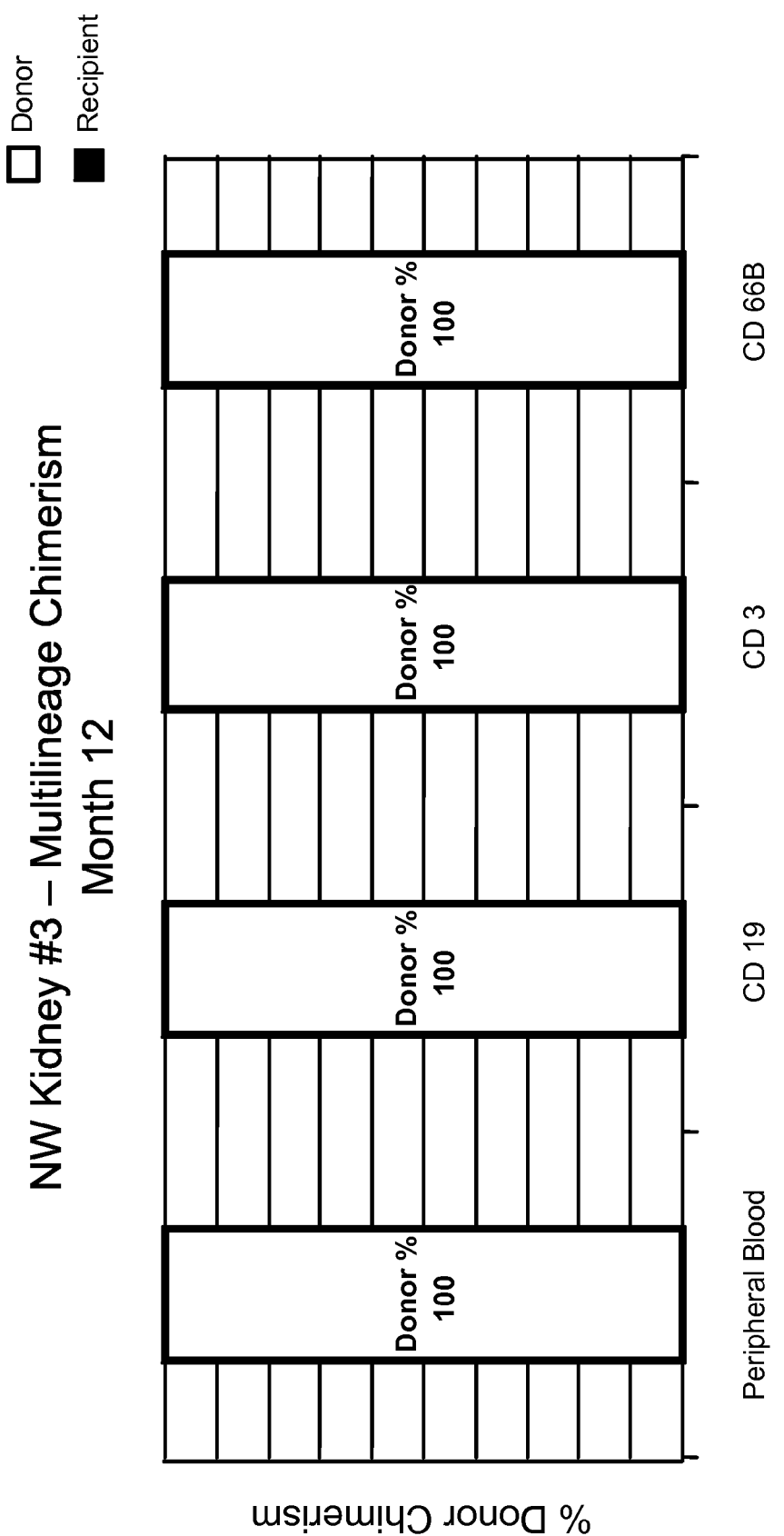
Figure 13C:
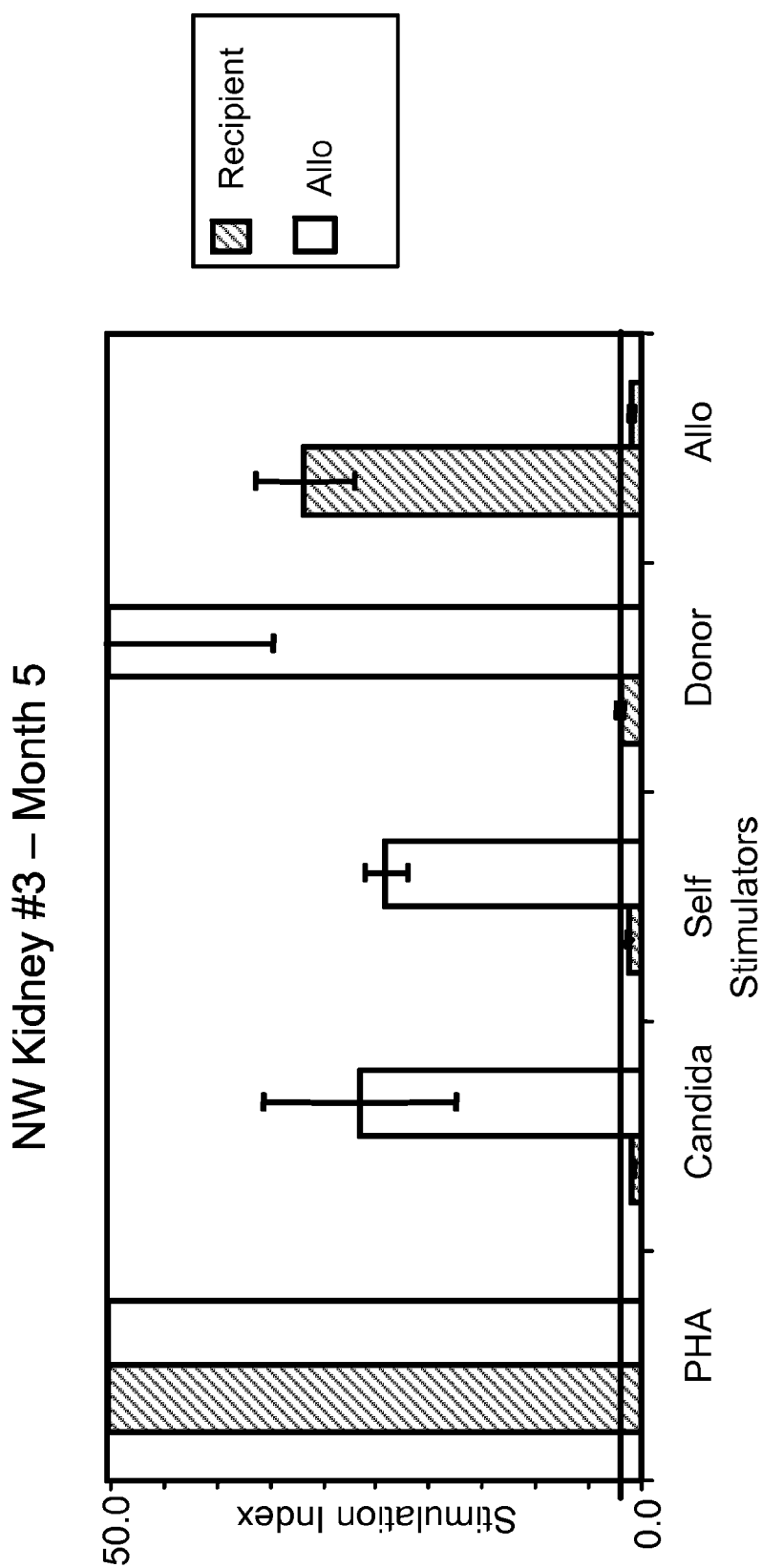
Figure 13D:
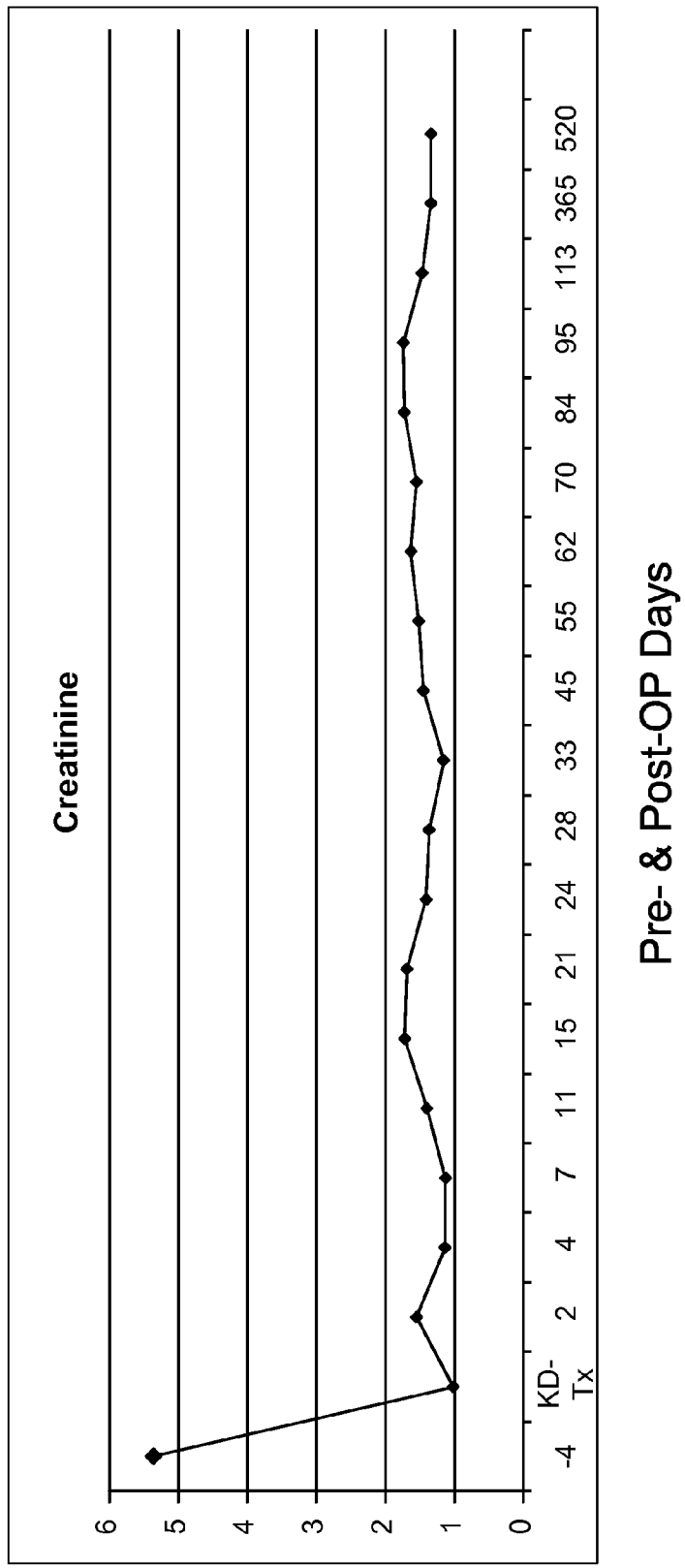
Figure 13E:
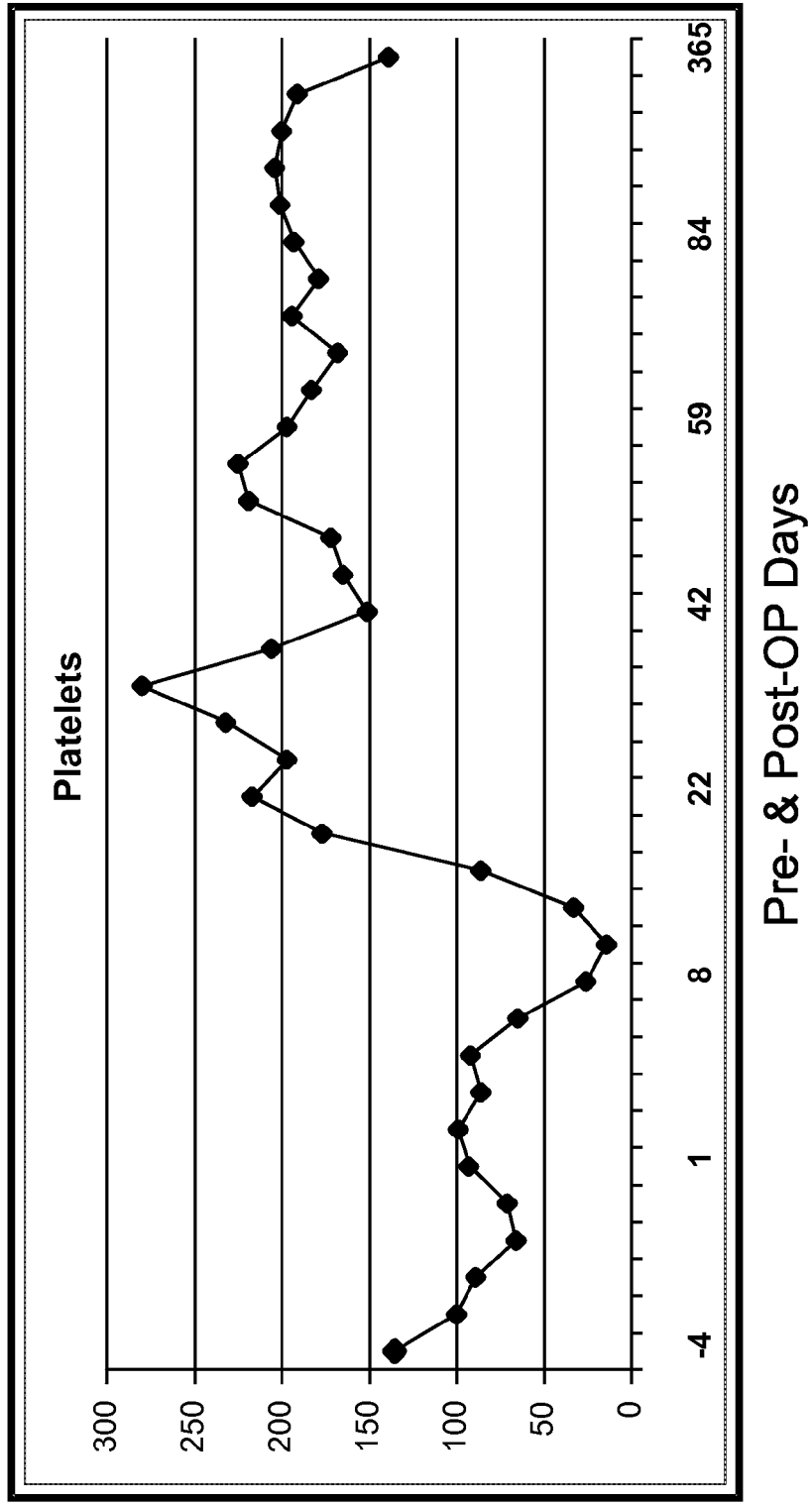
Figure 13F:
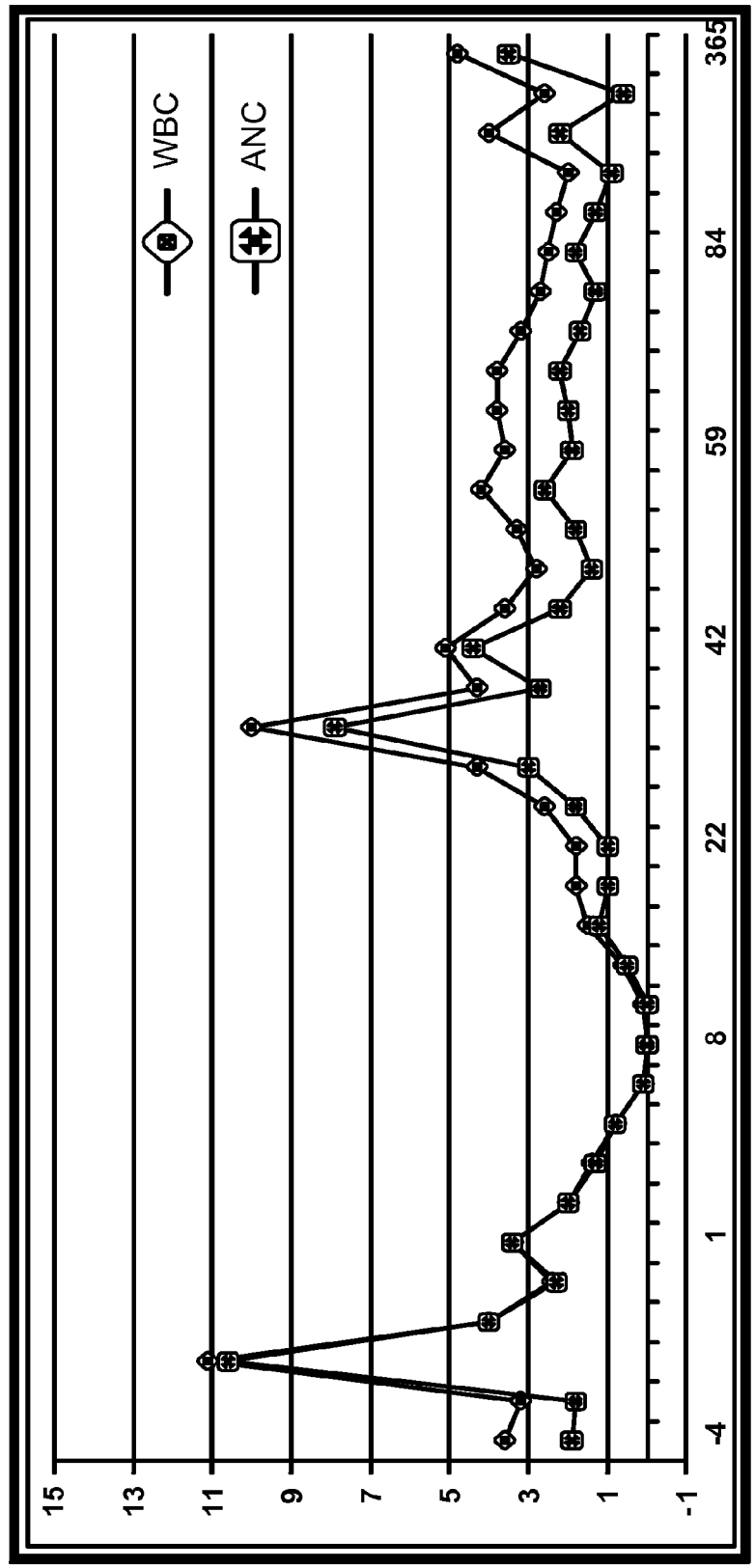

Subject #3 is a 43-year-old white male who developed ESRD due to polycystic kidney disease. A 1-of-6 HLA matched unrelated altruist was his donor. A total of $3.8 \times 10^6$ alpha beta $TCR^+$ T cells, $2.53 \times 10^6$ CD34 cells, and $4.48 \times 10^6$ FC/kg recipient body weight cryopreserved product were infused. The recipient demonstrated 95% donor chimerism at 1 month, and chimerism fluctuated between 63% and 100% over 18-months post-transplant (FIG. 13A). At 12 months, multilineage testing revealed 100% B cell, T cell, and myeloid production (FIG. 13B). Flow crossmatch was negative at 1 month and 6 months. At month 5, the recipient exhibited donor-specific tolerance and immunocompetence to respond to third-party alloantigen (FIG. 13C). This has persisted through 12 months. His renal function has remained stable based on creatinine output (FIG. 13D). The subject exhibited a transient nadir between 6-15 days (FIGS. 13E and 13F), which was managed as an outpatient.

Subject #5 is a 40-year-old male whose renal failure was secondary to chronic glomerulonephritis. He underwent a combined FC/renal transplant from a 1-of-6 HLA matched unrelated donor. His product was comprised of $3.8 \times 10^6$ alpha beta-$TCR^+$ T cells, $0.7 \times 10^6$ FC, and $3.94 \times 10^6$ CD34 cells/kg recipient body weight. The nadir followed a pattern similar to the prior subject. Chimerism was 100% at 1 month, 92% at 3 months, and 94% at month 5. A donor-specific tolerant profile began to emerge at month 3, with responses to PHA and third-party alloantigen but not to donor.

Subject #6 is a 39-year-old female who developed ESRD secondary to reflux. She underwent a second renal transplant from a 2-of-6 HLA matched unrelated donor. The product consisted of $3.8 \times 10^6$ alpha beta $TCR^+$ T cells, $8.59 \times 10^6$ $CD34^+$, and $3.11 \times 10^6$ FC cells/kg recipient body weight. The recipient exhibited 100% donor chimerism at 1 month.

TABLE 12

Summary of Kidney + hFC Patients

| Subject | Sex | Age | HLA Match | Date of Transplant | Original Disease | Adverse Events |
|---|---|---|---|---|---|---|
| 1 | M | 50 | 5/6 | February 2009 | Membranous | recurrent disease at 1-yr post-transplant; successfully treated with rituximab |
| 2 | M | 56 | 3/6 | April 2009 | Hypertension | febrile septic episode at 3-months post-transplant, marrow failure, autologous HSCT rescue, sepsis and allograft failure; now successfully re-transplanted with living donor kidney |
| 3 | M | 43 | 1/6 | May 2009 | PCKD | drug rash, shingles |

TABLE 12-continued

Summary of Kidney + hFC Patients

| Subject | Sex | Age | HLA Match | Date of Transplant | Original Disease | Adverse Events |
|---|---|---|---|---|---|---|
| 4 | M | 29 | 3/6 | June 2009 | Alports Syndrome | wound infection, sub-clinical rejection at one-year post-transplant |
| 5 | M | 40 | 1/6 | February 2010 | Chronic GN | flank cellulitis, wound seroma |
| 6 | F | 39 | 2/6 | March 2010 | Reflux: $2^{nd}$ Transplant | none |
| 7 | M | 35 | 3/6 | April 2010 | Hypertension | none |
| 8 | F | 46 | 1/6 | July 2010 | PCKD | i.v. site cellulitis |
| 9 | M | 28 | 0/6* | September 2010 | IgA Nephropathy | hemolytic uremic syndrome due to FK506, converted to sirolimus and resolved |

*1 minor antigen match

TABLE 13

Cell Dosing for Patients

| Patient | Source* | % chimerism at 1 month | Anti-donor Antibody Production | Composition delivered ($10^6$/kg recipient weight) | | |
|---|---|---|---|---|---|---|
| | | | | alpha beta T cells | CD34 | FC |
| 1 | IC* | 30 | No | 0.963 | .896 | 0.157 |
| 2 | MPB* | 95 | No | 3.8 | 2.53 | 4.48 |
| 3 | MPB | 100 | No | 3.8 | 3.6 | 0.90 |
| 4 | MPB | 25 | No | 1.94 | 1.00 | 0.49 |
| 5 | MPB | 100 | No | 3.8 | 3.94 | 0.716 |
| 6 | MPB | 100 | No | 3.8 | 8.59 | 3.11 |
| 7 | MPB | 100 | No | 3.8 | 16.9 | 1.16 |
| 8 | MPB | 100 | NA | 3.8 | 12.6 | 2.74 |
| 9 | MPB | 0 | NA | 3.8 | 5.07 | 2.12 |

*Source: IC, iliac crest marrow; MPB, mobilized peripheral blood

Example 8

Summary of hFC and Living Donor Kidney Transplant

Of the 9 subjects transplanted, the non-myeloablative conditioning was well-tolerated. In addition, the post-transplant nadir period for all subjects was easily managed as an outpatient.

Eight of the nine subjects demonstrated macrochimerism following transplantation, ranging from 6% to 100% at 1-month. Durable chimerism was achieved in the majority of subjects.

One subject has been weaned entirely off of immunosuppression. Several subjects have exhibited evidence of donor-specific hyporesponsiveness and are poised to be weaned from immunosuppression. Subjects were immunocompetent to respond to mitogen (PHA), *Candida*, and MHC-disparate third party alloantigen.

None of the subjects developed GVHD despite the HLA mistatching.

Section G. Metabolic Disorders

Example 1

Treatment of Inherited Metabolic Disorders

Subject #1 was a seven-year-old child with metachromatic leukodystrophy. He received a 3 out of 6 HLA-matched transplant from his father, who carries the trait for metachromatic leukodystrophy. The subject was conditioned essentially as described above in Section C, Example 2. He tolerated the conditioning and infusion very well as an outpatient. He received $14.4 \times 10^6$ CD34+ cells/kg body weight, $3.8 \times 10^6$ alpha beta TCR+ cells/kg body weight, and $4.1 \times 10^6$ FCs/kg body weight. His nadir was brief and he did not require transfusion therapy. His chimerism, by molecular STR, has ranged between 80%-98%. At 14 months post-transplant, the recipient exhibited no GVHD. The MLR results for this subject demonstrated tolerance to the donor and confirmed the likelihood of durable long term engraftment. Pre-transplant, the subject's Arylsulfatase A enzyme level was 3, compared to the donor's level of 50 post-transplantation. The subject's level was approximately 50 at three and six months post-transplant, and was 88.6 at one year post-transplant. This represents the enzyme level of a phenotypically normal patient.

Other Embodiments

It is to be understood that while the methods and compositions has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making a therapeutic human cellular composition for delivery to a recipient, comprising the steps of:
   providing a donor source of human hematopoietic stem cells (HSCs);
   depleting alpha beta TCR+T cells without significantly depleting HSCs or facilitating cells (FCs) from said donor source to produce a T cell-depleted donor source;
   adjusting the number of alpha beta TCR+T cells in said T cell-depleted donor source to between about $2.0 \times 10^6$ and about $5.0 \times 10^6$ alpha beta TCR+T cells per kg recipient body weight,
   thereby producing a therapeutic human cellular composition for delivery to a recipient.

2. The method of claim 1, wherein said source of human HSCs is bone marrow, thymus, peripheral blood, fetal liver, or embryonic yolk sac.

3. The method of claim 1, wherein said source of human HSCs is bone marrow.

4. The method of claim 1, wherein the cells are depleted using one or more antibodies.

5. The method of claim 4, wherein the one or more antibodies are conjugated to magnetic beads.

6. The method of claim 1, wherein the number of alpha beta TCR+T cells are adjusted to between about $3.0 \times 10^6$ and about $4.2 \times 10^6$ alpha beta TCR+T cells/kg recipient body weight.

7. The method of claim 1, wherein the therapeutic human cellular composition improves the engraftment ability of said human HSCs compared to human HSCs engrafted alone or in the absence of said therapeutic human cellular composition.

\* \* \* \* \*

UNITED STATES PATENT AND TRADEMARK OFFICE
CERTIFICATE OF CORRECTION

PATENT NO. : 8,632,768 B2  Page 1 of 1
APPLICATION NO. : 12/957011
DATED : January 21, 2014
INVENTOR(S) : Suzanne T. Ildstad It is certified that error appears in the above-identified patent and that said Letters Patent is hereby corrected as shown below:

In the Specification

Column 1, Lines 18-20, please delete "Grant No. 062016 awarded by the WM KECK Foundation and Grant No. W81XWH-07-0185 awarded by the Department of Defense Office of Army Research." and insert --W81XWH-07-1-0185 awarded by the Department of Defense (MRMC).--, therefor.

Signed and Sealed this
Twenty-seventh Day of May, 2014

Michelle K. Lee
*Deputy Director of the United States Patent and Trademark Office*